US010281820B2

(12) United States Patent
Kim et al.

(10) Patent No.: US 10,281,820 B2
(45) Date of Patent: May 7, 2019

(54) BLOCK COPOLYMER

(71) Applicant: LG Chem, Ltd., Seoul (KR)

(72) Inventors: Jung Keun Kim, Daejeon (KR); Je Gwon Lee, Daejeon (KR); Jeong Kyu Lee, Daejeon (KR); Se Jin Ku, Daejeon (KR); No Jin Park, Daejeon (KR); Mi Sook Lee, Daejeon (KR); Eun Young Choi, Daejeon (KR); Sung Soo Yoon, Daejeon (KR); Hyung Ju Ryu, Daejeon (KR)

(73) Assignee: LG Chem, Ltd. (KR)

( * ) Notice: Subject to any disclaimer, the term of this patent is extended or adjusted under 35 U.S.C. 154(b) by 232 days.

(21) Appl. No.: 15/515,818

(22) PCT Filed: Sep. 30, 2015

(86) PCT No.: PCT/KR2015/010335
§ 371 (c)(1),
(2) Date: Mar. 30, 2017

(87) PCT Pub. No.: WO2016/053011
PCT Pub. Date: Apr. 7, 2016

(65) Prior Publication Data
US 2017/0306139 A1    Oct. 26, 2017

(30) Foreign Application Priority Data

Sep. 30, 2014    (KR) .................. 10-2014-0131964
Dec. 8, 2014     (KR) .................. 10-2014-0175400
(Continued)

(51) Int. Cl.
*C08F 2/14*    (2006.01)
*C08F 32/06*   (2006.01)
(Continued)

(52) U.S. Cl.
CPC ............ *G03F 7/165* (2013.01); *B05D 1/005* (2013.01); *B05D 3/007* (2013.01);
(Continued)

(58) Field of Classification Search
CPC .. C08L 53/02; C08L 53/005; H01L 21/31056; C08G 61/12; G03F 7/165;
(Continued)

(56) References Cited

U.S. PATENT DOCUMENTS 3,976,672 A    8/1976    Strunk et al.
5,115,056 A    5/1992    Mueller et al.
(Continued)

FOREIGN PATENT DOCUMENTS

CN    1333790 A    1/2002
CN    1337974 A    2/2002
(Continued)

OTHER PUBLICATIONS

Anonymous., "Solid surface energy data (SFE) for common polymers", surface-tension.de, Feb. 2017, Retreived from the Internet: URL:http://www.surface-tension.de/solid-surface-energy.htm, XP002775246.
(Continued)

*Primary Examiner* — William K Cheung
(74) *Attorney, Agent, or Firm* — Lerner, David, Littenberg, Krumholz & Mentlik, LLP

(57) ABSTRACT

The present application relates to a block copolymer and uses thereof. The present application can provide a block copolymer—which exhibits an excellent self-assembling property and thus can be used effectively in a variety of applications—and uses thereof.

26 Claims, 13 Drawing Sheets

(30) Foreign Application Priority Data

| Dec. 8, 2014 | (KR) | 10-2014-0175401 |
|---|---|---|
| Dec. 8, 2014 | (KR) | 10-2014-0175402 |
| Dec. 8, 2014 | (KR) | 10-2014-0175406 |
| Dec. 8, 2014 | (KR) | 10-2014-0175407 |
| Dec. 8, 2014 | (KR) | 10-2014-0175410 |
| Dec. 8, 2014 | (KR) | 10-2014-0175411 |
| Dec. 8, 2014 | (KR) | 10-2014-0175412 |
| Dec. 8, 2014 | (KR) | 10-2014-0175413 |
| Dec. 8, 2014 | (KR) | 10-2014-0175414 |
| Dec. 8, 2014 | (KR) | 10-2014-0175415 |
| Jun. 4, 2015 | (KR) | 10-2015-0079490 |

(51) Int. Cl.

| C08F 212/08 | (2006.01) |
|---|---|
| C08F 216/12 | (2006.01) |
| C08F 220/26 | (2006.01) |
| C08F 220/30 | (2006.01) |
| C08F 293/00 | (2006.01) |
| C08J 5/18 | (2006.01) |
| C08L 53/00 | (2006.01) |
| C08L 53/02 | (2006.01) |
| C09D 153/00 | (2006.01) |
| G03F 7/16 | (2006.01) |
| C08G 61/12 | (2006.01) |
| H01L 21/3105 | (2006.01) |
| H01L 21/027 | (2006.01) |
| C08F 220/10 | (2006.01) |
| B05D 1/00 | (2006.01) |
| B05D 3/00 | (2006.01) |
| G03F 7/09 | (2006.01) |
| G03F 7/004 | (2006.01) |
| G03F 7/039 | (2006.01) |
| G03F 7/20 | (2006.01) |
| C08F 299/02 | (2006.01) |
| C08G 61/08 | (2006.01) |
| C08J 7/12 | (2006.01) |
| G03F 7/00 | (2006.01) |
| G03F 7/30 | (2006.01) |
| B81C 1/00 | (2006.01) |
| B82Y 40/00 | (2011.01) |

(52) U.S. Cl.
CPC ............ *B81C 1/00428* (2013.01); *C08F 2/14* (2013.01); *C08F 32/06* (2013.01); *C08F 212/08* (2013.01); *C08F 216/12* (2013.01); *C08F 220/10* (2013.01); *C08F 220/26* (2013.01); *C08F 220/30* (2013.01); *C08F 293/00* (2013.01); *C08F 293/005* (2013.01); *C08F 299/024* (2013.01); *C08G 61/08* (2013.01); *C08G 61/12* (2013.01); *C08J 5/18* (2013.01); *C08J 7/123* (2013.01); *C08L 53/00* (2013.01); *C08L 53/005* (2013.01); *C08L 53/02* (2013.01); *C09D 153/00* (2013.01); *G03F 7/0002* (2013.01); *G03F 7/0046* (2013.01); *G03F 7/039* (2013.01); *G03F 7/091* (2013.01); *G03F 7/16* (2013.01); *G03F 7/162* (2013.01); *G03F 7/2004* (2013.01); *G03F 7/30* (2013.01); *H01L 21/0273* (2013.01); *H01L 21/31055* (2013.01); *H01L 21/31056* (2013.01); *H01L 21/31058* (2013.01); *B81C 2201/0149* (2013.01); *B82Y 40/00* (2013.01); *C01P 2002/70* (2013.01); *C07B 2200/00* (2013.01); *C08F 2220/301* (2013.01); *C08F 2438/03* (2013.01); *C08G 2261/1424* (2013.01); *C08G 2261/1426* (2013.01); *C08G 2261/332* (2013.01); *C08G 2261/3324* (2013.01); *C08G 2261/40* (2013.01); *C08G 2261/418* (2013.01); *C08J 2353/00* (2013.01)

(58) Field of Classification Search
CPC .... C08F 212/08; C08F 216/12; C08F 220/10; C08F 220/30; C08F 293/005; C08F 32/06; C08F 299/024; C08F 293/00; C08F 2/14; C08J 5/18; C08J 2353/00; C08J 7/123
USPC ......................................................... 526/72
See application file for complete search history.

(56) References Cited

U.S. PATENT DOCUMENTS

| 5,202,402 A | 4/1993 | Funaki et al. |
|---|---|---|
| 5,234,604 A | 8/1993 | Liao et al. |
| 5,391,626 A | 2/1995 | Machida et al. |
| 5,418,290 A | 5/1995 | Machida et al. |
| 5,554,695 A | 9/1996 | Machida et al. |
| 5,728,431 A | 3/1998 | Bergbreiter et al. |
| 6,025,437 A | 2/2000 | Hirahara et al. |
| 6,314,225 B1 | 11/2001 | Wang |
| 6,531,547 B1 | 3/2003 | Visger et al. |
| 6,546,282 B1 | 4/2003 | Inoue et al. |
| 6,953,649 B2 | 10/2005 | Prat et al. |
| 7,538,159 B2 | 5/2009 | Wang et al. |
| 8,163,189 B2 | 4/2012 | Iyoda et al. |
| 8,211,737 B2 | 7/2012 | Russell et al. |
| 8,791,042 B2 | 7/2014 | Ronan et al. |
| 9,495,991 B2 | 11/2016 | Han et al. |
| 2003/0143343 A1 | 7/2003 | Kawabata et al. |
| 2004/0049836 A1 | 3/2004 | Ashraf et al. |
| 2004/0110856 A1 | 6/2004 | Young et al. |
| 2004/0143032 A1 | 7/2004 | Auschra et al. |
| 2004/0242787 A1 | 12/2004 | Chun et al. |
| 2006/0166033 A1 | 7/2006 | Poetsch et al. |
| 2006/0172082 A1 | 8/2006 | Masuda |
| 2007/0142559 A1 | 6/2007 | Wang et al. |
| 2007/0166648 A1 | 7/2007 | Ponoth et al. |
| 2007/0219338 A1 | 9/2007 | Takeda et al. |
| 2008/0105854 A1 | 5/2008 | Huh et al. |
| 2008/0193658 A1 | 8/2008 | Millward |
| 2008/0213556 A1 | 9/2008 | Cha et al. |
| 2008/0286333 A1 | 11/2008 | Kangas et al. |
| 2008/0311402 A1 | 12/2008 | Jung et al. |
| 2009/0114108 A1 | 5/2009 | Oya et al. |
| 2009/0240001 A1 | 9/2009 | Regner |
| 2009/0253867 A1 | 10/2009 | Takahashi et al. |
| 2009/0306295 A1 | 12/2009 | Mays et al. |
| 2010/0086801 A1 | 4/2010 | Russell et al. |
| 2010/0098876 A1 | 4/2010 | Hanson |
| 2010/0102415 A1 | 4/2010 | Millward et al. |
| 2010/0120985 A1 | 5/2010 | Konishi et al. |
| 2010/0155988 A1 | 6/2010 | Keil et al. |
| 2010/0206057 A1 | 8/2010 | Batchelder et al. |
| 2010/0210742 A1 | 8/2010 | Iyoda et al. |
| 2010/0216312 A1 | 8/2010 | Yamamoto et al. |
| 2010/0266957 A1 | 10/2010 | Harada et al. |
| 2010/0285276 A1 | 11/2010 | Kim et al. |
| 2010/0286351 A1 | 11/2010 | Yoshida et al. |
| 2010/0305230 A1 | 12/2010 | Li et al. |
| 2011/0186544 A1* | 8/2011 | Endou ............... B29C 71/02 216/58 |
| 2011/0253946 A1 | 10/2011 | Huh et al. |
| 2011/0294070 A1 | 12/2011 | Hatakeyama et al. |
| 2012/0052446 A1 | 3/2012 | Jaycox et al. |
| 2012/0116024 A1 | 5/2012 | Iyoda et al. |
| 2012/0214094 A1 | 8/2012 | Mikoshiba et al. |
| 2013/0048488 A1 | 2/2013 | Shufflebotham |
| 2013/0078576 A1 | 3/2013 | Wu et al. |
| 2013/0183828 A1 | 7/2013 | Nakamura et al. |
| 2013/0189504 A1 | 7/2013 | Nealey et al. |

(56) References Cited

U.S. PATENT DOCUMENTS

| | | | |
|---|---|---|---|
| 2013/0209693 A1 | 8/2013 | Vogel et al. |
| 2013/0209755 A1 | 8/2013 | Hustad et al. |
| 2013/0248488 A1 | 9/2013 | Han et al. |
| 2013/0284698 A1 | 10/2013 | Ogihara |
| 2013/0306594 A1 | 11/2013 | Hustad et al. |
| 2014/0011916 A1 | 1/2014 | Lee et al. |
| 2014/0127456 A1 | 5/2014 | Regner |
| 2014/0141375 A1 | 5/2014 | Cho et al. |
| 2014/0238954 A1 | 8/2014 | Matsumiya et al. |
| 2014/0370442 A1 | 12/2014 | Ober et al. |
| 2015/0064630 A1 | 3/2015 | Wuister et al. |
| 2015/0085042 A1 | 3/2015 | Keoshkerian et al. |
| 2015/0197663 A1 | 7/2015 | Mizutani et al. |
| 2015/0228298 A1 | 8/2015 | Han et al. |
| 2016/0204653 A1 | 7/2016 | Lee |
| 2016/0257838 A1 | 9/2016 | Senzaki et al. |
| 2016/0280823 A1 | 9/2016 | Kim et al. |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 103797066 A | 5/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| CN | 107075052 A | 8/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2006212477 A | 8/2006 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010116466 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012036078 A | 2/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014078014 A | 5/2014 |
| JP | 2014102503 A | 6/2014 |
| JP | 2014160770 | 9/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |

(56) References Cited

FOREIGN PATENT DOCUMENTS

| | | |
|---|---|---|
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067069 A | 6/2015 |
| KR | 20150067070 A | 6/2015 |
| KR | 20160038705 A | 4/2016 |
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015084129 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

Cummins et al., "Solvothermal Vapor Annealing of Lamellar Poly(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Beng H. Tan et al., "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, 2009, vol. 30, pp. 1002-1008.
Chinese Search Report for CN Application No. 201480074044.7 dated Jun. 7, 2018.
Frank S. Bates et al., "Block Copolymer Thermodyanmics: Theory and Experiment", Annu. Rev. Phys. Chem., 1990, vol. 41, pp. 525-557.
G.R. Strobl, "The Physics of Polymers: Concepts for Understanding Their Structures and Behavior", Springer (Abstract Only).
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Extended European Search Report including Written Opinion for Application No. EP15845665.7 dated Jun. 27, 2018.
Katja Nilles et al., "Raft Polymerization of Activated 4-Vinylbenzoates"., Journal of Polymer Science: Part A: Polymer Chemistry, Jan. 1, 2009, vol. 47, pp. 1696-1705.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly( N, N-diethylacrylamide) Block Copolymer Aqueous Solutions: Evidence of Premicellar Aggregates" Journal of Physical Chemistry Part B: Condensed Matter, Materials, Surfaces, Interfaces & Biophysical, vol. 114, No. 31, Aug. 12, 2010 (Aug. 12, 2010), 9977-9986, XP055394763, US ISSN: 1520-6106, DOI: 10.1021/jp101613y * abstract* * Scheme 1, PDcA11-block-PDEA295; p. 9978 *.
Database CA [Online] Chemical Abstracts Service Ohio US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998]* abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 DOI: 10.1002/macp. 200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)"Macromolecules American Chemical Society US vol. 27 No. 15 Jul. 18, 1994 (Jul. 18, 1994) pp. 4093-4100 XP000456650 ISSN: 0024-9297 DOI: 10.1021/MA00093A010 * abstract *.
Chinese Search Report for Application No. CN201580059758.5 dated Sep. 5, 2018.
Chinese Search Report for Application No. CN201580060097.8 dated Sep. 19, 2018.

(56) References Cited

OTHER PUBLICATIONS

Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extended European Seach Report including Written Opinion for EP Application No. 15847574.9, dated May 3, 2018.
Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP15846832.2 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,293, filed Mar. 29, 2017.
U.S. Appl. No. 15/515,432, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,821, filed Mar. 30, 2017.
CN Search Report for Application No. CN201580059710.4. dated Sep. 3, 2018.
Extended European Search Report including Written Opinion for EP Application 15846126.9 dated Sep. 12, 2018.
Kobayashi S, Matsuzawa T, Matsuoka SI, Tajima H, Ishizone T. Living Anionic Polymerizations of 4-(1-Adamantyl) styrene and 3-(4-Vinylphenyl)-1, 1'-biadamantane. Macromolecules. Sep. 5, 2006;39(18):5979-5986.
EESR for EP Application No. 15847536.8 dated Aug. 23, 2018, 6 pages.
Chinese Search Report for Application No. 201480072759.9 dated Jan. 24, 2018.
Naoko Kihara., "Self-Organizing Lithography Technology", Toshiba Review, Apr. 1, 2012, vol. 67, No. 4, pp. 44-47 (Abstract Only).
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Supplementary European Search Report for EP15847157 dated Mar. 21, 2018.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
Hua et al. "Temperature-induced phase-transitions of methoxyoligo(oxyethylene) styrene-based block copolymers in aqueous solution", Soft Matter, 2013, 9, 8897.
International Search Report from PCT/KR2014/012023, dated Mar. 10, 2015.
International Search Report from PCT/KR2014/012024, dated Mar. 17, 2015.
International Search Report from PCT/KR2014/012025, dated Mar. 17, 2015.
International Search Report from PCT/KR2014/012026, dated Mar. 17, 2015.
International Search Report from PCT/KR2014/012027, dated Mar. 17, 2015.
International Search Report from PCT/KR2014/012028, dated Mar. 17, 2015.
International Search Report from PCT/KR2014/012029, dated Mar. 17, 2015.
International Search Report from PCT/KR2014/012030, dated Mar. 17, 2015.
International Search Report from PCT/KR2014/012031, dated Feb. 12, 2015.
International Search Report from PCT/KR2014/012032, dated Feb. 12, 2015.
International Search Report from PCT/KR2014/012033, dated Feb. 12, 2015.
International Search Report from PCT/KR2014/012034, dated Feb. 12, 2015.
International Search Report from PCT/KR2014/012035, dated Feb. 12, 2015.
International Search Report from PCT/KR2014/012036, dated Mar. 17, 2015.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.

(56) References Cited

OTHER PUBLICATIONS

International Search Report from PCT/KR2015/010327, dated Jan. 12, 2016.
International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 103142745, dated Dec. 14, 2015.
IPO Search Report from Taiwan Application No. 103142777, dated Dec. 15, 2015.
IPO Search Report from Taiwan Application No. 103142780, dated Dec. 15, 2015.
IPO Search Report from Taiwan Application No. 103142784, dated Jan. 27, 2016.
IPO Search Report from Taiwan Application No. 103142786, dated Jan. 11, 2016.
IPO Search Report from Taiwan Application No. 103142790, dated Dec. 15, 2015.
IPO Search Report from Taiwan Application No. 103142794, dated Dec. 15, 2015.
IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 84, 021710 (2011).
Park et al., "Block Copolymer Lithography: Periodic Arrays of ~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.

\* cited by examiner

BLOCK COPOLYMER

CROSS-REFERENCE TO RELATED APPLICATIONS

The present application is a national phase entry under 35 U.S.C. § 371 of International Application No. PCT/KR2015/010335, filed Sep. 30, 2015, published in Korean, which claims priority to and the benefit of Korean Patent Application No. 2014-0131964, filed on Sep. 30, 2014, No. 2015-0079490, filed on Jun. 4, 2015, No. 2014-0175411, filed on Dec. 8, 2014, No. 2014-0175414, filed on Dec. 8, 2014, No. 2014-0175410, filed on Dec. 8, 2014, No. 2014-0175415, filed on Dec. 8, 2014, No. 2014-0175412, filed on Dec. 8, 2014, No. 2014-0175413, filed on Dec. 8, 2014, No. 2014-0175407, filed on Dec. 8, 2014, No. 2014-0175406, filed on Dec. 8, 2014, No. 2014-0175400, filed on Dec. 8, 2014, No. 2014-0175401, filed on Dec. 8, 2014, and No. 2014-0175402, filed on Dec. 8, 2014, the disclosures of which are incorporated herein by reference in their entirety.

FIELD

The present application relates to a block copolymer and uses thereof.

BACKGROUND

The block copolymer has a molecular structure in which polymer blocks each with a distinct chemical structure are connected to one another by covalent bonds. The block copolymer can be constructed in a structure such as a sphere, a cylinder and a lamella through phase separation. The structure that is formed as the result of the self-assembly phenomenon of a block copolymer has a domain whose size can be adjusted over a wide range, and it can be constructed in various forms which can be applied to the production of a variety of next-generation nanodevices, magnetic storage media, and patterns (by lithography or the like): to be specific, the production of high-density magnetic recording media, nanowires, quantum dots, metal dots or the like.

DESCRIPTION

Object

The present application provides block copolymers, polymer films, methods of forming a polymer film, and methods of forming a pattern.

Solution

An illustrative block copolymer may contain a block 1 and a block 2, which is different from the block 1. Each block in the block copolymer may be made up of only one type of a monomer, or it may be made up of two or more types of monomers. The block copolymer may be a diblock copolymer which contains each one of the block 1 and block 2 only. The block copolymer may also be a triblock or multiblock (with more than three types of blocks) copolymer which contains, in addition to each one of the block 1 and block 2, either one or both of the block 1 and block 2, either exclusively or together with another type(s) of block(s).

A block copolymer contains 2 or more polymer chains which are connected to one another by a covalent bond(s), thus phase separation occurs to form a so-called self-assembled structure. The inventors have recognized that, when a block copolymer satisfies any one, two or more of the conditions provided below in the present specification, the aforementioned phase separation occurs more effectively and, accordingly, the formation of a nanoscale structure becomes possible as a result of microphase separation. Therefore, the present application relates to a block copolymer that satisfies at least one of the conditions provided below in the present specification. The form or size of the nanoscale structure can be controlled, for example, by the size (i.e. molecular weight or the like) of the block copolymer or relative ratios among the blocks. In this way, the block copolymer of the present application is capable of forming, without constraint, a phase-separated structure such as a sphere, a cylinder, a gyroid, a lamella and an inverted structure of various sizes. The conditions will be described simply one after another, and none of the conditions will take precedence over the others. The block copolymer may satisfy any one, two or more conditions that are selected among the conditions described below in the present specification. It has been recognized that the block copolymer can have a self-assembling property by satisfying any one of the conditions. In the present application, the term "vertical orientation" refers to the direction in which a block copolymer is oriented and may indicate that the nanostructure formed by the block copolymer is oriented vertically to the direction of a substrate; for example, the interface between the domain formed by the block 1 of the block copolymer and the domain formed by the block 2 of the same block copolymer may be vertical to the surface of the substrate. In the present application, errors are accounted for in the term "vertical"; for example, the definition of this term may include an error within the range of ±10 degrees, ±8 degrees, ±6 degrees, ±4 degrees, or ±2 degrees.

Technology for controlling the self-assembled structure of a block copolymer either horizontally or vertically on a variety of substrates accounts for a remarkably large part in a practical application of block copolymers. The orientation of a nanostructure in a block copolymer film is generally determined by which block among the blocks constituting the block copolymer is exposed to the surface or in the air. In general, the majority of substrates are polar and the air is nonpolar; therefore, the blocks having higher polarities among the blocks that constitute a block copolymer are seen as being in contact with a substrate, and the blocks having lower polarities are seen as being in contact with the interface with the air. Therefore, there are a variety of techniques proposed to make blocks, each with distinct properties, of a block copolymer which enables wetting at the substrate side simultaneously, the most representative of all is to prepare a neutral surface to control the orientation.

The inventors have identified that, when a block copolymer is prepared to satisfy any one, two or more, or all of the conditions described below in the present specification, the block copolymer can be vertically oriented also on a substrate that had not been previously treated by any method—such as surface neutralization—that is well known in the art to achieve vertical orientation.

For example, a block copolymer of one aspect of the present application can exhibit vertical orientation both on a hydrophilic surface and on a hydrophobic surface, both of which have not undergone any particular pre-treatment.

Also, in another aspect of the present application, vertical orientation as the above can be induced within a short time over a large area through thermal annealing.

Accordingly, an illustrative block copolymer of the present application contains the block 1 and the block 2, each with a distinct chemical structure, can form a film that produces a grazing-incidence small-angle X-ray scattering (GISAXS) in-plane diffraction pattern on a surface that has a room-temperature wetting angle of 50 degrees to 70 degrees against purified water, and can form a film that produces a GISAXS in-plane diffraction pattern also on a surface that has a room-temperature wetting angle of 5 degrees to 20 degrees against purified water (Condition 1).

Another illustrative block copolymer of the present application contains the block 1 and the block 2, each with a distinct chemical structure, where the block 1 or the block copolymer as a whole can produce a peak in the azimuthal angle range of −90 degrees to −70 degrees and also in the azimuthal angle range of 70 degrees to 90 degrees in a diffraction pattern of a grazing-incidence wide-angle X-ray scattering (GIWAXS) spectrum, where the scattering vector q ranges from 12 $nm^{-1}$ to 16 $nm^{-1}$ (Condition 2).

Another illustrative block copolymer of the present application contains the block 1 and the block 2, each with a distinct chemical structure, where the block 1 or the block copolymer as a whole can produce a melting transition peak or an isotropic transition peak at a temperature of −80° C. to 200° C. during differential scanning calorimetry (DSC) analysis (Condition 3).

Another illustrative block copolymer of the present application contains the block 1 and the block 2, each with a distinct chemical structure, where the block 1 or the block copolymer as a whole can produce a peak with the full width at half maximum (FWHM) of 0.2 to 0.9 $nm^{-1}$ in the scattering vector q range of 0.5 $nm^{-1}$ to 10 $nm^{-1}$ during XRD analysis (Condition 4).

Another illustrative block copolymer of the present application contains the block 1 and the block 2, each with a distinct chemical structure, where the block 1 contains a side chain, and both the number n of chain-forming atoms in the side chain and the scattering vector q obtained as the result of XRD analysis on the block 1 can satisfy the following Mathematical Expression 2 (Condition 5).

$$3\ nm^{-1}\ to\ 5\ nm^{-1}=nq/(2\times\pi)\qquad\text{[Mathematical Expression 2]}$$

In Mathematical Expression 2, n represents the number of chain-forming atoms in the aforementioned side chain, and q represents—during the XRD analysis on a block that contains the side chain—either the smallest scattering vector q whose peak is detectable or the scattering vector q that is observed to have the peak with the largest peak area.

Another illustrative block copolymer of the present application contains the block 1 and the block 2, each with a distinct chemical structure, and the absolute value of the difference in surface energies between the block 1 and the block 2 can be 10 mN/m or less (Condition 6).

Another illustrative block copolymer of the present application contains the block 1 and the block 2, each with a distinct chemical structure, and the absolute value of the difference in densities between the block 1 and the block 2 can be 0.25 $g/cm^3$ or more (Condition 7).

Another illustrative block copolymer of the present application contains the block 1 and the block 2, each with a distinct chemical structure, and the X that is calculated according to the following Mathematical Expression A can have a range of 1.25 or more (Condition 8). In this case, the block copolymer can form a so-called lamella structure.

$$X=1+(D\times M)/(K\times L)\qquad\text{[Mathematical Expression A]}$$

In Mathematical Expression A, D represents the ratio D2/D1 of the density D2 of the second block to the density D1 of the first block; M represents the ratio M1/M2 of the molar mass M1 of the first block to the molar mass M2 of the second block; K represents the ratio A2/A1 in a $^1$H-NMR spectrum of the area A2 of the peak that is produced based on the second block to the area A1 of the peak that is produced based on the first block; and L represents the ratio H1/H2 of the number H1 of hydrogen atoms in 1 mole of the repeat unit of the first block to the number H2 of hydrogen atoms in 1 mole of the repeat unit of the second block.

In each of the above block copolymers, the block 1 may be a block that contains a side chain that will be described in detail below in the present specification.

Hereinafter, the aforementioned conditions will be described in further detail.

A. Condition 1

The block copolymer of the present application can form a film that produces a GISAXS in-plane diffraction pattern on a hydrophobic surface and on a hydrophilic surface. In the present application, producing an in-plane diffraction pattern during GISAXS may refer to having peaks that are vertical to the x-component in a GISAXS diffraction pattern during GISAXS analysis. Such peaks are observed due to vertical orientation of a block copolymer. Therefore, a block copolymer producing an in-plane diffraction pattern indicates vertical orientation. In another example, the number of the aforementioned peaks that are observed on the x-component of a GISAXS diffraction pattern may be at least 2, and when multiple peaks are present, the scattering vectors q of the peaks may be identified to have integer ratios, in which case, the phase separation efficiency of the block copolymer can be further improved.

The block copolymer capable of forming a film that produces an in-plane diffraction pattern both on a hydrophilic surface and on a hydrophobic surface can exhibit vertical orientation on a variety of surfaces that had not been previously treated by any particular method to induce vertical orientation. In the present application, the term "a hydrophilic surface" refers to a surface whose wetting angle against purified water is in the range of 5 degrees to 20 degrees. Examples of a hydrophilic surface may include, but are not limited to, the surface of silicon that is surface-treated with oxygen plasma, sulfuric acid or piranha solution. In the present application, the term "a hydrophobic surface" refers to a surface whose room-temperature wetting angle against purified water is in the range of 50 degrees to 70 degrees. Examples of a hydrophobic surface may include, but are not limited to, the surface of polydimethylsiloxane (PDMS) that is surface-treated with oxygen plasma, the surface of silicon that is surface-treated with hexamethyldisilazane (HMDS), and the surface of silicon that is surface-treated with hydrogen fluoride (HF).

Unless specifically indicated otherwise, the properties (e.g. wetting angle or density) that may change depending on the temperature in the present application are numerical values that are measured at room temperature. The term "room temperature" refers to the temperature in its natural state, which has not undergone heating or cooling, and may refer to a temperature of about 10° C. to 30° C., about 25° C., or about 23° C.

The film that is formed on a hydrophilic or hydrophobic surface and produces an in-plane diffraction pattern during GISAXS may be a film that has undergone thermal annealing. The film for a GISAXS measurement may be formed, for example, by applying a solution—that is prepared by dissolving the above block copolymer at a concentration of about 0.7 wt % in a solvent (e.g. flourobenzene)—on the corresponding hydrophilic or hydrophobic surface at a thickness of about 25 nm and a coating area of 2.25 $cm^2$ (width: 1.5 cm, length: 1.5 cm) and thermal-annealing the coated layer. The thermal annealing may be carried out, for example, by allowing the above film to be maintained at a temperature of about 160° C. for about 1 hour. GISAXS may be measured by having an X-ray incident on a film, which is prepared in the aforementioned manner, at an angle of incidence in the range of about 0.12 to 0.23 degrees. A diffraction pattern that is scattered from the film can be obtained by a measuring device (e.g. 2D marCCD) that is well-known in the art. The method of using the diffraction pattern to verify the presence or absence of an in-plane diffraction pattern is well known in the art.

The block copolymer that is observed to have the aforementioned peaks during GISAXS can exhibit an excellent self-assembling property, which can also be controlled effectively depending on the purpose.

B. Condition 2

Any one block of the block copolymer of the present application can produce a peak both in an azimuthal angle range of −90 degrees to −70 degrees and in an azimuthal angle range of 70 degrees to 90 degrees in a diffraction pattern of a GIWAXS spectrum, where the scattering vector q ranges from 12 $nm^{-1}$ to 16 $nm^{-1}$. The above peak may be produced by a block that contains a side chain described below in the present specification. In the present specification, the block 1 may be the aforementioned block that contains a side chain. In the above description, an azimuthal angle refers to the azimuthal angle that is determined by setting an angle, which is measured relative to the upward direction of a diffraction pattern (i.e. the direction of the out-of-plane diffraction), as 0 degrees and is measured in a clockwise direction. In other words, the angle has a positive value when measured in a clockwise direction, and it has a negative value when measured in a counterclockwise direction. The FWHM of a peak that is observed in each of the aforementioned azimuthal angle ranges may range from 5 degrees to 70 degrees. In another example, the FWHM may be 7 degrees or more, 9 degrees or more, 11 degrees or more, 13 degrees or more, 15 degrees or more, 17 degrees or more, 19 degrees or more, 21 degrees or more, 25 degrees or more, 30 degrees or more, 35 degrees or more, 40 degrees or more, or 45 degrees or more. In another example, the FWHM may also be 65 degrees or less, or 60 degrees or less. The method of obtaining a GIWAXS spectrum is not particularly limited, and the spectrum may be obtained by a method that is described in an example below in the present specification. The peak profile of a diffraction pattern of the obtained spectrum may be subject to Gaussian fitting, and the FWHM can be obtained from the fitted result. When only a half of the Gaussian-fitted result is observed, the FWHM may be defined as twice the value that is obtained from the observed half of the result. The R-square of Gaussian fitting ranges from 0.26 to 0.95. In other words, it is sufficient if the aforementioned FWHM is observed when R-square falls in the above range. The method of obtaining the information such as the above is well known in the art; for example, a numerical analysis program, such as Origin, may be used.

GIWAXS may be performed on a polymer that is made up of only a monomer that constitutes the block to be measured. The block that satisfies the Condition 2 may contain an aromatic structure without a halogen atom that will be described below in the present specification, or it may contain a side chain. The block that produces the above peak at the aforementioned azimuthal angle of GIWAXS can possess an orientation property in arrangement and, when used in combination with one or more other types of blocks, can exhibit excellent phase separation, self-assembly and vertical orientation.

C. Condition 3

The block copolymer of the present application—or any one block of the block copolymer—can produce a melting transition peak or an isotropic transition peak at a temperature of −80° C. to 200° C. during DSC analysis. When any one block of a block copolymer behaves as the above during DSC analysis and the block copolymer, to which the above block is contained, satisfies both Condition 2 and Condition 3, the block (that behaves as the above during DSC analysis) may be a block that produces the GIWAXS peak previously described in Condition 2 (i.e. a peak that appears both in an azimuthal angle range of −90 degrees to −70 degrees and in an azimuthal angle range of 70 degrees to 90 degrees in a diffraction pattern of a GIWAXS spectrum, where the scattering vector q ranges from 12 $nm^{-1}$ to 16 $nm^{-1}$) and may be, for example, the block 1. A block copolymer—or any one block of the block copolymer—may produce either one or both of a melting transition peak and an isotropic transition peak. In this case, the block copolymer may be a copolymer that contains a block that has a crystal phase and/or a liquid crystal phase—both of which are suitable for self-assembly—or the block copolymer itself may have a crystal phase and/or a liquid crystal phase throughout the molecular structure.

The block copolymer—or any one block of the block copolymer—that behaves as the above during DSC may further satisfy the following Condition 3.

For example, when both the isotropic transition peak and melting transition peak appear, the temperature Ti at which the isotropic transition peak appears may be different from the temperature Tm at which the melting transition peak appears by 5° C. to 70° C. In another example, the difference Ti−Tm in the temperatures may be 10° C. or more, 15° C. or more, 20° C. or more, 25° C. or more, 30° C. or more, 35° C. or more, 40° C. or more, 45° C. or more, 50° C. or more, 55° C. or more, or 60° C. or more. When the difference Ti−Tm between the isotropic transition peak temperature Ti and the melting transition peak temperature Tm falls within the above range, the phase separation or self-assembly of the block copolymer or (in the case that the description corresponds to a specific block and not to a block copolymer as a whole) of the block copolymer that contains such a block can be maintained at an excellent level.

In another example, when both the isotropic transition peak and the melting transition peak are produced, the ratio M/I of the area I of the isotropic transition peak to the area M of the melting transition peak may be in the range of 0.1 to 500. When the ratio M/I of the area I of the isotropic transition peak to the area M of the melting transition peak falls within the above range, the phase separation or self-assembly of the block copolymer or (in the case that the description corresponds to a specific block and not to a block copolymer as a whole) of the block copolymer that contains such a block can be maintained at an excellent level. In another example, the ratio M/I may be 0.5 or more, 1 or more, 1.5 or more, 2 or more, 2.5 or more, or 3 or more. Also, in another example, the ratio M/I may be 450 or less, 400 or less, 350 or less, 300 or less, 250 or less, 200 or less, 150 or less, 100 or less, 90 or less, or 85 or less.

The methods of conducting DSC analysis are well known in the art, and any one of the methods well known in the art may be used to carry out the analysis in the present application.

The melting transition peak may appear in a temperature Tm range of −10° C. to 55° C. In another example, the Tm may be 50° C. or less, 45° C. or less, 40° C. or less, 35° C.

or less, 30° C. or less, 25° C. or less, 20° C. or less, 15° C. or less, 10° C. or less, 5° C. or less, or 0° C. or less.

As will be described below in further detail in the present specification, a block copolymer may contain a block that contains a side chain. In this case, the block copolymer may satisfy the following Mathematical Expression 1.

10° C.≤$Tm$−12.25° C.×$n$+149.5° C.≤ 10° C.　　　　　[Mathematical Expression 1]

In Mathematical Expression 1, Tm represents the temperature at which a melting transition peak of the above block copolymer or of the block that has the above side chain appears, and n represents the number of chain-forming atoms in the above side chain.

The block copolymer that satisfies the above mathematical expression can exhibit excellent phase separation or an excellent self-assembling property.

In another example, Tm−12.25° C.×n+149.5° C. in Mathematical Expression 1 may be calculated as about −8° C. to 8° C., about −6° C. to 6° C., or about −5° C. to 5° C.

D. Condition 4

The block copolymer of the present application may contain a block that produces at least one peak within a predetermined range of a scattering vector q during X-ray diffraction (XRD) analysis. When a block copolymer satisfies Condition 4 in addition to aforementioned Condition 2 and/or Condition 3, the block (of the block copolymer) that satisfies Condition 2 and/or Condition 3 may also satisfy Condition 4. The block that satisfies Condition 4 may be the aforementioned block 1.

For example, any one block in the above block copolymer may have at least one peak in the scattering vector q range of 0.5 $nm^{-1}$ to 10 $nm^{-1}$ during XRD analysis. In another example, the scattering vector q at which the above peak(s) appear(s) may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another example, the scattering vector q at which the above peak(s) appear(s) may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less. The full width at half maximum (FWHM) of the peak(s) that is/are observed within the above scattering vector q range may be in the range of 0.2 to 0.9 $nm^{-1}$. In another example, the above FWHM may be 0.25 $nm^{-1}$ or more, 0.3 $nm^{-1}$ or more, or 0.4 $nm^{-1}$ or more. Also, in another example, the above FWHM may be 0.85 $nm^{-1}$ or less, 0.8 $nm^{-1}$ or less, or 0.75 $nm^{-1}$ or less.

In Condition 4, the term "full width at half maximum" may refer to the width (i.e. the difference between the two extreme scattering vector q values) of the largest peak at half the maximum amplitude.

The above scattering vector q and FWHM in XRD analysis are numerical values obtained by a numerical analytical method that applies least-squares regression on the XRD analytical result. In the above method, the part that corresponds to the minimum intensity in an XRD diffraction pattern is set as the baseline and the minimum intensity is set as zero, then the peak profile of the above XRD pattern is subject to Gaussian fitting, and the aforementioned scattering vector q and FWHM are obtained from the fitted result. When the above Gaussian fitting is performed, the R-square value is at least 0.9 or more, 0.92 or more, 0.94 or more, or 0.96 or more. The method of obtaining the information from XRD analysis, as mentioned above, is well-known in the art; for example, a numerical analysis program, such as Origin, may be used.

The block copolymer that produces a peak that has the aforementioned FWHM value in the aforementioned scattering vector q range can have a crystalline region that is suitable for self-assembly. The block copolymer that is identified in the aforementioned scattering vector q range can exhibit an excellent self-assembling property.

XRD analysis may be carried out by transmitting X-rays through a block copolymer specimen and then measuring the scattering intensity with respect to a scattering vector. XRD analysis may be conducted by using the polymer that is prepared by polymerizing only the monomer that constitutes any one block (e.g. the block 1) of a block copolymer. XRD analysis may be carried out on such a block copolymer without requiring any particular pretreatment; for example, it may be conducted by drying the block copolymer under a suitable condition and then transmitting X-rays through it. An X-ray whose vertical size is 0.023 mm and horizontal size is 0.3 mm may be used. The scattering vector and FWHM may be obtained through the acquisition of the 2D diffraction pattern—that is scattered from the specimen—in the form of an image by using a measuring device (e.g. 2D marCCD) and the fitting of the acquired diffraction pattern in the aforementioned method.

E. Condition 5

The block copolymer of the present application can contain, as the block 1, a block that contains a side chain as described below in the present specification, and the number n of chain-forming atoms in the side chain and the scattering vector q that is obtained by XRD analysis conducted by a method as described in aforementioned Condition 4 may satisfy the following Mathematical Expression 2.

3 $nm^{-1}$ to 5 $nm^{-1}$=$nq/(2×π)$　　　　　[Mathematical Expression 2]

In Mathematical Expression 2, n represents the number of the aforementioned chain-forming atoms, and q represents the smallest scattering vector q whose peak is detectable, or the scattering vector q that is observed to have the peak with the largest peak area, during the XRD analysis on the aforementioned block that contains a side chain. In addition, π represents the ratio of the circumference of a circle to its diameter in Mathematical Expression 1.

The q and the like of Mathematical Expression 2 are numerical values that are obtained in the same manner as in the description of the aforementioned XRD analysis method.

The q of Mathematical Expression 2 may be, for example, a scattering vector q in the range of 0.5 $nm^{-1}$ to 10 $nm^{-1}$. In another example, the scattering vector q of Mathematical Expression 2 may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another example, the scattering vector q of Mathematical Expression 2 may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less.

Mathematical Expression 2 describes the relationship between the distance D among the blocks that contain the aforementioned chain and the number of chain-forming atoms, when the block copolymer is self-assembled to form a phase-separated structure. When the number of chain-forming atoms in the block copolymer containing the aforementioned chain satisfies Mathematical Expression 2, the crystallinity of the chain increases, and thereby the phase separation or vertical orientation property can significantly improve. In another example, $nq/(2×π)$ in Mathematical Expression 2 may be 4.5 $nm^{-1}$ or less. In the above description, the distance D (in the unit of nm) among the blocks containing the above chain can be calculated by using the Mathematical Expression, $D=2×π/q$, where D represents the above distance D (in the unit of nm) among the blocks, and π and q are as defined in Mathematical Expression 2.

F. Condition 6

In the block copolymer of the present application, the absolute value of the difference between the surface energy of the block 1 and the surface energy of the block 2 in a block copolymer may be 10 mN/m or less, 9 mN/m or less, 8 mN/m or less, 7.5 mN/m or less, or 7 mN/m or less. Also, the absolute value of the difference between the above surface energies may be 1.5 mN/m, 2 mN/m, or 2.5 mN/m or more. The structure in which the block 1 and block 2, which have an absolute value of the difference in surface energies in the above range, are connected to each other by covalent bonds can induce microphase separation as the result of phase separation due to a sufficient level of immiscibility. In the above description, the block 1 may be, for example, a block that contains a side chain as described below in the present specification, or, it may be, for example, a block that contains an aromatic structure that does not contain a halogen atom.

A surface energy may be measured by using the Drop Shape Analyzer DSA100 (manufactured by KRUSS GmbH). Specifically, the surface energy may be measured on the film prepared by applying a coating solution—which is prepared by dissolving the subject specimen to be measured (i.e. a block copolymer or a homopolymer) in fluorobenzene to a solid concentration of about 2 wt %—on a substrate at a thickness of about 50 nm and a coating area of 4 cm² (width: 2 cm, length: 2 cm), drying at room temperature for about 1 hour, and then thermal-annealing at 160° C. for about 1 hour. The process of measuring a contact angle by dropping deionized water, whose surface tension is well-known in the art, on the above thermal-annealed film is repeated for 5 times, and the 5 measured values of a contact angle are averaged. Similarly, the process of measuring a contact angle by dropping diiodomethane, whose surface tension is well-known in the art, on the above thermal-annealed film is repeated for 5 times, and the 5 measured values of a contact angle are averaged. Subsequently, the surface energies can be obtained by using the averaged values of the contact angle, which were measured respectively with deionized water and diiodomethane, and substituting the numerical value (Strom value) that corresponds to the surface tension of a solvent into the Mathematical Expressions according to the Owens-Wendt-Rabel-Kaelble method. The numerical value that corresponds to the surface energy of each block of a block copolymer can be obtained by using the above-described method on a homopolymer that is made up of only the monomers that constitute the above block.

When a block copolymer contains the aforementioned side chain, the block in which the side chain is contained can have a surface energy that is higher than that of the other block. For example, when a block copolymer contains a side chain in the block 1, the surface energy of the block 1 may be higher than that of the block 2. In this case, the surface energy of the block 1 may be in the range of about 20 mN/m to 40 mN/m. The surface energy of the block 1 may be 22 mN/m or more, 24 mN/m or more, 26 mN/m or more, or 28 mN/m or more. Also, the surface energy of the block 1 may be 38 mN/m or less, 36 mN/m or less, 34 mN/m or less, or 32 mN/m or less. A block copolymer in which such a block 1 is contained and has a surface energy that is different from that of the block 2 as described above can exhibit an excellent self-assembling property.

G. Condition 7

In a block copolymer, the absolute value of the difference in densities between the block 1 and block 2 may be 0.25 g/cm³ or more, 0.3 g/cm³ or more, 0.35 g/cm³ or more, 0.4 g/cm³ or more, or 0.45 g/cm³ or more. The aforementioned absolute value of the difference in densities may be 0.9 g/cm³ or more, 0.8 g/cm³ or less, 0.7 g/cm³ or less, 0.65 g/cm³ or less, or 0.6 g/cm³ or less. The structure in which the block 1 and block 2 have the absolute value of the difference in densities within the above range and are connected to each other by covalent bonds may induce an effective microphase separation as the result of phase separation due to a sufficient level of immiscibility.

The density of each block in the above block copolymer can be measured by using a buoyancy method that is well-known in the art; for example, the density can be measured by analyzing the mass of the block copolymer in a solvent, such as ethanol, whose mass and density in air are known.

When the block copolymer contains the aforementioned side chain, the block in which the side chain is contained may have a density that is lower than that of the other block(s). For example, when the block copolymer contains a side chain inside the block 1, the block 1 may have a lower density compared to the block 2. In this case, the density of the block 1 may be in the range of about 0.9 g/cm³ to 1.5 g/cm³. The density of the block 1 may be 0.95 g/cm³ or more. Also, the density of the block 1 may be 1.4 g/cm³ or less, 1.3 g/cm³ or less, 1.2 g/cm³ or less, 1.1 g/cm³ or less, or 1.05 g/cm³ or less. The block copolymer in which the above block 1 is contained and has a density that is different from that of the block 2 as described above can exhibit an excellent self-assembling property.

H. Condition 8

In the block copolymer of the present application, the value of X that is calculated by the following Mathematical Expression A may be, for example, 1.25 or more. The block copolymer in which the value of X (that is calculated by the following Mathematical Expression A) is 1.25 or more may be a diblock copolymer that is made up of only the block 1 and the block 2.

$$X=1+(D \times M)/(K \times L) \quad \text{[Mathematical Expression A]}$$

In Mathematical Expression A, D represents the ratio D2/D1 of the density D2 of the second block to the density D1 of the first block; M represents the ratio M1/M2 of the molar mass M1 of the first block to the molar mass M2 of the second block; K represents the ratio A2/A1 in a $^1$H-NMR spectrum of the area A2 of the peak that is produced based on the second block to the area A1 of the peak that is produced based on the first block; and L represents the ratio H1/H2 of the number H1 of hydrogen atoms in 1 mole of the repeat unit of the first block to the number H2 of hydrogen atoms in 1 mole of the repeat unit of the second block.

There is no particular limitation to the method of conducting $^1$H-NMR to obtain the value of K that is substituted in Mathematical Expression A, and any method well known in the art can be used. One example of the above method is described in the example section below in the present specification. The method of calculating a peak area from the NMR result is well known in the art. For example, the ratio of peak areas can be simply calculated from the area of each peak when, by looking at the NMR result, the peaks derived from each of the block 1 and block 2 do not overlap each other; in contrast, when the peaks overlap each other, the ratio of the peaks is calculated, taking the overlapped part into consideration. There are various interpretation programs known in the field to calculate a peak area through an interpretation of a $^1$H-NMR spectrum; for example, a MestReC program can be used to calculate a peak area.

The density of each block of a block copolymer, which is required to obtain the value of D that is substituted in Mathematical Expression A, can be measured by using a buoyancy method that is well known in the art. For example, the density can be measured by analyzing the mass of the block copolymer that is immersed in a solvent—such as ethanol—whose mass and density in air are known. The density of a block can be measured, for example, by subjecting a homopolymer—that is made up of only the monomer that constitutes the above block—to a buoyancy method.

As described above, the value of M that is substituted in Mathematical Expression A corresponds to the ratio of molar masses of repeat units of blocks in a block copolymer. The molar masses can be obtained in any method that is well known in the art; for example, the value of M can be obtained as the ratio of molar masses of monomers that make up blocks in a block copolymer. In this case, when any one of the blocks in the block copolymer is made up of two or more types of monomers, the molar mass of the monomer that is most abundant (in terms of number of moles)—among the above two or more types of monomers—in the above block can be substituted for the value of the molar mass that is required to calculate the value of M.

As described above, the value of L that is substituted in the Mathematical Expression A corresponds to the ratio of numbers of hydrogen atoms that 1 mole of block repeat units of a block copolymer contains. The above ratio can also be obtained based on the chemical structure of each repeat unit; for example, the ratio can be obtained from the number of hydrogen atoms in the chemical structure of the monomer constituting each block of a block copolymer or by $^1$H-NMR. Also in this case, when any one of the blocks in a block copolymer is made up of two or more types of monomers, the molar mass of the monomer that is most abundant (in terms of number of moles)—among the above two or more types of monomers—in the above block can be substituted for the value of the molar mass that is required to calculate the value of L.

The X of Mathematical Expression A is a numerical value that represents the amount ratio between the block 1 and block 2 in a block copolymer. The proportion of each block in a block copolymer is normally measured based on the molecular weight that is obtained based on gel permeation chromatography (GPC) or the like. However, the inventors recognized that, with the above general method being used, the ratio among the blocks was not correctly reflected and, thus, the method failed to realize the block copolymer as originally designed. For example, GPC alone cannot identify the occasional failure in the synthesis of a block copolymer (which contains each of its blocks at a respective target level) that occurs depending on the reactivity of the macroinitiator and monomers when the synthesis is intended by using any one block of the block copolymer as the macroinitiator as will be described below in the present specification.

In another example, the X of Mathematical Expression A may be about 1.3 or more, about 1.35 or more, about 1.4 or more, about 1.45 or more, about 1.5 or more, about 1.6 or more, or about 1.65 or more. In another example, the X of Mathematical Expression A may also be 10 or less, 9.5 or less, 9 or less, 8.5 or less, 8 or less, 7.5 or less, or 7 or less.

In another example, the X of Mathematical Expression A may be in the range of about 2.5 to 6.7, about 2.5 to 5, or about 2.8 to 5. When the value of X falls within the above range, the block copolymer can form a so-called cylindrical structure or a self-assembled structure in which the cylindrical structure is predominant. In another example, the X of Mathematical Expression A may also be about 1.65 to 2.5, about 1.8 to 2.5, or about 1.8 to 2.3. When the value of X falls within the above range, the block copolymer can form a so-called lamella structure or a self-assembled structure in which the lamella structure is predominant.

For example, when the above block 1 is a block that contains an aromatic structure without a halogen atom and is contained in a block copolymer together with the block 2 that is substituted in part by one or more halogen atoms—or when the block 1 is a block that contains a side chain and is contained in a block copolymer together with the block 2 that contains one or more halogen atoms—as described below in the present specification, the block copolymer in which the value of X falls within the aforementioned range can effectively form a vertically oriented structure.

As described above in the present specification, the block copolymer may satisfy any one, two or more conditions that are selected among the aforementioned Conditions 1 to 8.

For example, the block copolymer may be a block copolymer that satisfies Condition 1, Condition 2, Condition 3, Condition 4, Condition 5, Condition 6, Condition 7, or Condition 8.

In one example, the above block copolymer may contain the block 1 (that satisfies any one, two or more of Conditions 2 to 5 among the aforementioned conditions) and the block 2, where the difference in surface energies of the blocks is as described in Condition 6.

In another example, the above block copolymer may contain the block 1 (that satisfies any one, two or more of Conditions 2 to 5) and the block 2, satisfying the ratio of the block 1 to block 2 as described in Condition 8, where the difference in surface energies of the blocks is as described in Condition 6.

Without intending to be limited by theory, the block 1 that satisfies any one of Conditions 2 to 5 can have a property of a crystal or liquid crystal, and, therefore, it can be regularly packed during the formation of a self-assembled structure. In this case, when the block 1 and the block 2 satisfy Condition 6 in terms of the difference in surface energies, the domains formed by each of the block 1 and block 2 are substantially neutralized and, therefore, the self-assembled film can be vertically oriented, regardless of the property of the surface on which the film is formed. When the aforementioned ratio of blocks satisfies the value of X in Condition 8, the effect of the above neutralization is maximized, and thus, the effect of vertical orientation is also maximized.

As an additional condition, the number average molecular weight (Mn) of a block copolymer may be, for example, in the range of 3,000 to 300,000. In the present specification, the term "a number average molecular weight" refers to a numerical value that is measured with GPC and calibrated based on a standard polystyrene, and, unless specifically indicated otherwise, the term "a molecular weight" in the present specification refers to a number average molecular weight. In another example, Mn may be, for example, 3000 or more, 5000 or more, 7000 or more, 9000 or more, 11000 or more, 13000 or more, or 15000 or more. In still another example, Mn may be about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. A block copolymer may have a polydispersity (Mw/Mn) in the range of 1.01 to 1.60. In another example, the Mw/Mn may be about 1.1 or more, about 1.2 or more, about 1.3 or more, or about 1.4 or more.

In such a range, a block copolymer can exhibit a sufficient self-assembling property. The Mn and the like of a block copolymer can be adjusted in consideration of the self-assembled structure of interest and the like.

The aforementioned conditions may be achieved, for example, by controlling the structure of a block copolymer. For example, either one or both of the block 1 and block 2 of a block copolymer that satisfies one or more of the above conditions may include at least an aromatic structure. Both the block 1 and block 2 may each include an aromatic structure; in this case, the aromatic structure included in any one of the block 1 or block 2 may be identical to or different from the aromatic structure in the other block. In addition, at least one among the block 1 and block 2 of a block copolymer that satisfies one or more of the above conditions may contain an aforementioned side chain or one or more halogen atoms which will be described below in the present specification, and the side chain and halogen atom(s) may be substituted for one or more parts of the above aromatic structures. The block copolymer of the present application may contain two or more blocks.

As described above, the block 1 and/or block 2 of the above block copolymer may each include an aromatic structure. The aromatic structure is included in either one or both of the block 1 and block 2. When each of the two types of blocks includes an aromatic structure, the aromatic structure included in one type of block may be identical to or different from that in the other type of block.

In the present specification, the term "an aromatic structure" may refer to the structure of an aromatic compound, "an aryl group" may refer to a monovalent residue that is derived from an aromatic compound, and "an arylene group" may refer to a divalent residue that is derived from an aromatic compound. Unless specifically indicated otherwise, "an aromatic compound" in the above description refers to a compound that contains a benzene ring or two or more benzene rings (which are connected to one another either by sharing one or two carbon atoms or by any linker), or it refers to a derivative of the compound. Therefore, the above aryl group, which is a monovalent residue that is derived from an aromatic compound, may refer to a substituent in which radicals that are formed as a hydrogen atom breaks away from the aromatic compound are covalently bonded, and the above arylene group, which is a divalent residue that is derived from an aromatic compound, may refer to a substituent in which radicals that are formed as two hydrogen atoms break away from the aromatic compound are covalently bonded. The above aryl group or arylene group may be an aryl group or arylene group with, for example, 6 to 30 carbons, 6 to 25 carbons, 6 to 21 carbons, 6 to 18 carbons, or 6 to 13 carbons. An illustrative aryl group or arylene group may also be a monovalent or divalent residue that is derived from benzene, naphthalene, azobenzene, anthracene, phenanthrene, tetracene, pyrene, benzopyrene, or the like.

The above aromatic structure may be a structure that is included in the main chain of a block, or it may be a structure that is connected, in the form of a side chain, to the main chain of a block. By suitably controlling the aromatic structure that can be contained in each block, the aforementioned conditions can be controlled.

In one example, a block copolymer that satisfies one or more of the aforementioned conditions may contain the block 1 (that contains a side chain) and the block 2 that is different from the block 1. In the above description, the side chain may be a side chain that contains 8 or more chain-forming atoms, as will be described below in the present specification. In this case, the block 1 may be a block that satisfies any one, two or more, or all of the aforementioned conditions 2, 3, 4 and 5.

The above block 1 may contain a ring structure, and the above side chain may be substituted for one or more parts of the ring structure. The ring structure may be the aforementioned aromatic structure (i.e. an aryl group or an arylene group) or an alicyclic ring structure. In this case, the ring structure may be a ring structure that does not contain a halogen atom.

In the present specification, the term "an alicyclic ring structure" refers to, unless specifically indicated otherwise, a ring-type hydrocarbon atom structure other than an aromatic ring structure. An alicyclic ring structure may be contained in a block copolymer in the form of a monovalent residue or a divalent residue. Unless specifically indicated otherwise, the above alicyclic ring structure may refer to an alicyclic ring structure with, for example, 3 to 30 carbons, 3 to 25 carbons, 3 to 21 carbons, 3 to 18 carbons, or 3 to 13 carbons.

The block 2 that is contained in a block copolymer together with the above block 1 is a block that is chemically different from the block 1. The above block 2 may be a block that contains a halogen atom, for example, a chlorine atom or a fluorine atom. The above block 2 may contain 1 or more, 2 or more, 3 or more, 4 or more or 5 or more halogen atoms. The number of the halogen atoms may also be, for example, 30 or less, 25 or less, 20 or less, 15 or less, 10 or less, 9 or less, 8 or less, 7 or less, 6 or less, or 5 or less. The above block 2 may include a ring structure, and the ring structure may be substituted in part by the above halogen atom(s). The above ring structure may be the aforementioned aromatic structure, which is an aryl group or an arylene group.

In the present application, the term "a side chain" refers to a chain that is connected to the main chain of a polymer, and the term "a chain-forming atom" refers to an atom that forms the above side chain of a block copolymer and, in other words, an atom that forms a linear structure of the side chain. The side chain may be a linear-type or a branched-type, but the number of chain-forming atoms is counted only by the number of atoms that form the longest linear chain, and the other atoms that are bonded to the above chain-forming atoms (e.g. when the chain-forming atom is a carbon atom, the hydrogen atom or the like that is bonded to the carbon atom) are not taken into account. For example, in the case of a branched-type chain, the number of chain-forming atoms may be counted by the number of chain-forming atoms that form the longest chain. For example, when the side chain is an n-pentyl group, all of the chain-forming atoms are carbon and the number of the chain-forming atoms is five, and also when the side chain is a 2-methylpentyl group, all of the chain-forming atoms are carbon and the number of the chain-forming atoms is 5. Examples of a chain-forming atom may include carbon, oxygen, sulfur, and nitrogen; a suitable chain-forming atom may be any one of carbon, oxygen and nitrogen, or any one of carbon and oxygen. The number of chain-forming atoms in a chain may be 8 or more, 9 or more, 10 or more, 11 or more, or 12 or more. The number of chain-forming atoms in a chain may also be 30 or less, 25 or less, 20 or less, or 16 or less.

The aforementioned condition(s) can be controlled by including, in the block 1 of a block copolymer, a chain with 8 or more chain-forming atoms as a side chain connected to the block. The terms "a chain" and "a side chain" may refer to a common object in the present specification.

As mentioned above, a side chain may be a chain that contains 8 or more, 9 or more, 10 or more, 11 or more or 12 or more chain-forming atoms. The number of the chain-forming atoms in a side chain may also be 30 or less, 25 or less, 20 or less, or 16 or less. Each of the chain-forming atoms may be any one of carbon, oxygen, nitrogen and sulfur, or it may suitably be any one of carbon and oxygen.

A hydrocarbon chain such as an alkyl group, an alkenyl group and an alkynyl group may be exemplified as the side chain. At least one carbon atom in the above hydrocarbon chain may each be substituted by a sulfur atom, an oxygen atom, or a nitrogen atom.

When the side chain is connected to a ring structure such as an aromatic structure, the chain may be connected to the ring structure either directly or by a linker. Examples of the linker may include an oxygen atom, a sulfur atom, —NR$_1$—, —S(=O)$_2$—, a carbonyl group, an alkylene group, an alkenylene group, an alkynylene group, —C(=O)—X$_1$— and —X$_1$—C(=O)—, where the R$_1$ may represent a hydrogen atom, an alkyl group, an alkenyl group, an alkynyl group, an alkoxy group or an aryl group, and the X$_1$ may represent a single bond, an oxygen atom, a sulfur atom, —NR$_2$—, —S(=O)$_2$—, an alkylene group, an alkenylene group or an alkynylene group, where the R$_2$ may represent a hydrogen atom, an alkyl group, an alkenyl group, an alkynyl group, an alkoxy group, or an aryl group. An oxygen atom may be exemplified as a suitable linker. The side chain may be connected to an aromatic structure, for example, by an oxygen atom or a nitrogen atom.

When the aforementioned ring structure such as an aromatic structure is connected (in the form of a side chain) to the main chain of a block, the above aromatic structure may also be connected to the main chain either directly or by a linker. In this case, examples of the linker may include an oxygen atom, a sulfur atom, —S(=O)$_2$—, a carbonyl group, an alkylene group, an alkenylene group, an alkynylene group, —C(=O)—X$_1$— or —X$_1$—C(=O)—, where the X$_1$ may represent a single bond, an oxygen atom, a sulfur atom, —S(=O)$_2$—, an alkylene group, an alkenylene group or an alkynylene group. Examples of a suitable linker that connects an aromatic structure to the main chain may include, but are not limited to, —C(=O)—O— and —O—C(=O)—.

In another example, the aromatic structure that is included in the block 1 and/or block 2 of a block copolymer may contain 1 or more, 2 or more, 3 or more, 4 or more or 5 or more halogen atoms. The number of the halogen atoms may also be, for example, 30 or less, 25 or less, 20 or less, 15 or less, or 10 or less. Examples of the halogen atom may include fluorine and chlorine, and it may be advantageous to use fluorine. Such a block that includes an aromatic structure with one or more halogen atoms can efficiently realize a phase-separated structure by having sufficient interactions with other block(s).

An illustrative aromatic structure that contains one or more halogen atoms may be an aromatic structure with 6 to 30 carbons, 6 to 25 carbons, 6 to 21 carbons, 6 to 18 carbons or 6 to 13 carbons, although it is not limited thereto.

When both the block 1 and block 2 of a block copolymer include an aromatic structure, to realize a sufficient level of phase separation in the structure, the block 1 may be set to include an aromatic structure without a halogen atom while the block 2 is set to include an aromatic structure with one or more halogen atoms. In addition, the aforementioned side chain may be connected to the aromatic structure of the above block 1, either directly or by a linker that contains oxygen or nitrogen.

When a block copolymer contains a block with a side chain, the block may be, for example, a block that is represented by the following Structural Formula 1. The above block may be a block that contains the structural unit represented by the following Structural Formula 1 as a main component. In the present specification, a block containing a particular structural unit as a main component may refer to the case in which the block contains the structural unit at 60% or more, 70% or more, 80% or more, 90% or more or 95% or more based on weight or the case in which the structural unit is contained in the block in the proportion of 60 mol % or more, 70 mol % or more, 80 mol % or more, 90 mol % or more, or 95 mol % or more.

[Structural Formula 1]

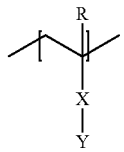

In Structural Formula 1, R represents a hydrogen atom or an alkyl group with 1 to 4 carbons; X represents a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, where the X$_1$ represents an oxygen atom, a sulfur atom, —S(=O)$_2$—, an alkylene group, an alkenylene group or an alkynylene group; and Y represents a monovalent substituent that includes a ring structure to which the aforementioned side chain with 8 or more chain-forming atoms is connected.

In the present application, the term "a single bond" may refer to an absence of any particular atom in the corresponding area. For example, in the case that the X of Structural Formula 1 represents a single bond, a structure having the Y connected directly to the polymer chain can be realized.

Unless specifically indicated otherwise, the term "an alkyl group" in the present specification may refer to a linear-type, branched-type or ring-type alkyl group with 1 to 20 carbons, 1 to 16 carbons, 1 to 12 carbons, 1 to 8 carbons or 1 to 4 carbons, which may be optionally substituted in part by one or more substituents (however, when the aforementioned side chain refers to an alkyl group, the alkyl group may contain 8 or more, 9 or more, 10 or more, 11 or more or 12 or more carbon atoms, where the number of carbon atoms in the alkyl group may also be 30 or less, 25 or less, 20 or less, or 16 or less).

Unless specifically indicated otherwise, the term "an alkenyl group" or "an alkynyl group" in the present specification may refer to a linear-type, branched-type or ring-type alkenyl group or alkynyl group with 2 to 20 carbons, 2 to 16 carbons, 2 to 12 carbons, 2 to 8 carbons or 2 to 4 carbons, which may be optionally substituted in part by one or more substituents (however, the alkenyl group or alkynyl group as the aforementioned side chain may contain 8 or more, 9 or more, 10 or more, 11 or more or 12 or more carbon atoms, where the number of carbon atoms in the alkenyl group or alkynyl group may also be 30 or less, 25 or less, 20 or less, or 16 or less).

Unless specifically indicated otherwise, the term "an alkylene group" in the present specification may refer to a linear-type, branched-type or ring-type alkylene group with 1 to 20 carbons, 1 to 16 carbons, 1 to 12 carbons, 1 to 8 carbons or 1 to 4 carbons, which may be optionally substituted in part by one or more substituents.

Unless specifically indicated otherwise, the terms "an alkenylene group" or "an alkynylene group" in the present specification may refer to a linear-type, branched-type or ring-type alkenylene group or alkynylene group with 1 to 20 carbons, 1 to 16 carbons, 1 to 12 carbons, 1 to 8 carbons or 1 to 4 carbons, which may be optionally substituted in part by one or more substituents.

In another example, the X of Structural Formula 1 may also represent —C(=O)O— or —OC(=O)—.

The Y of Structural Formula 1 represents a substituent, which contains the aforementioned side chain, that may be, for example, a substituent that includes an aromatic structure with 6 to 18 carbons or 6 to 12 carbons. The above chain may be, for example, a linear-chain alkyl group with 8 or more, 9 or more, 10 or more, 11 or more or 12 or more carbon atoms. The alkyl group may also contain 30 or less, 25 or less, 20 or less or 16 or less carbon atoms. The above chain may be connected to the above aromatic structure either directly or by an aforementioned linker.

In another example, the block 1 structural unit that is represented by the above Structural Formula 1 may also be represented by the following Structural Formula 2.

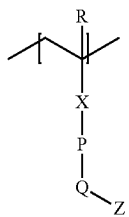

[Structural Formula 2]

In Structural Formula 2, R represents a hydrogen atom or an alkyl group with 1 to 4 carbons, X represents —C(=O)—O—, P represents an arylene group with 6 to 12 carbons, Q represents an oxygen atom, and Z represents an aforementioned side chain with 8 or more chain-forming atoms.

In another example, the P of Structural Formula 2 may represent a phenylene, and, in another example, the Z may represent a linear-chain alkyl group with 9 to 20 carbons, 9 to 18 carbons, 9 to 16 carbons, 10 to 16 carbons, 11 to 16 carbons, or 12 to 16 carbons. When the P represents a phenylene, the Q may be connected in the para position of the above phenylene. The above alkyl group, arylene group, phenylene group and side chain may be optionally substituted in part by one or more substituents.

When a block copolymer contains a block that includes an aromatic structure with one or more halogen atoms—for example, the block 2—the block may be exemplified by a block that contains the structural unit represented by the following Structural Formula 3. In this case, the structural unit represented by the following Structural Formula 3 may be contained in the block as a main component.

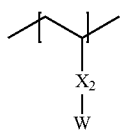

[Structural Formula 3]

In Structural Formula 3, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ represents a single bond, an oxygen atom, a sulfur atom, —S(=O)$_2$—, an alkylene group, an alkenylene group or an alkynylene group; and W represents an aryl group with at least one halogen atom.

In another example, the $X_2$ of Structural Formula 3 may represent a single bond or an alkylene group.

In Structural Formula 3, the aryl group that is represented by W may be an aryl group with 6 to 12 carbons or a phenyl group, where the aryl group or phenyl group may contain 1 or more, 2 or more, 3 or more, 4 or more or 5 or more halogen atoms. The number of the halogen atoms may also be, for example, 30 or less, 25 or less, 20 or less, 15 or less, or 10 or less. For the halogen atom, a fluorine atom may be exemplified.

In another example, the structural unit represented by Structural Formula 3 may also be represented by the following Structural Formula 4.

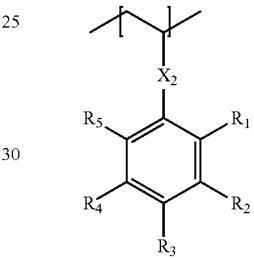

[Structural Formula 4]

In Structural Formula 4, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ represents a single bond, an oxygen atom, a sulfur atom, —S(=O)$_2$—, an alkylene group, an alkenylene group or an alkynylene group; and each of $R_1$ to $R_5$ independently represents hydrogen, an alkyl group, a haloalkyl group or a halogen atom, where one or more halogen atoms are contained in the positions marked as $R_1$ to $R_5$.

In Structural Formula 4, each of $R_1$ to $R_5$ independently represents a hydrogen atom, an alkyl group with 1 to 4 carbons, a haloalkyl group with 1 to 4 carbons, or a halogen, where the halogen may be chlorine or fluorine.

In Structural Formula 4, 2 or more, 3 or more, 4 or more, 5 or more or 6 or more among $R_1$ to $R_5$ may each represent a halogen. There is no particular limitation to the maximum number of the above halogen atoms; it may be, for example, 12 or less, 8 or less, or 7 or less.

As mentioned earlier in the present specification, a block copolymer may be a diblock copolymer that contains any two of the aforementioned structural units, or it may be a block copolymer that contains another type(s) of block(s) in addition to either one or both of the aforementioned two types of blocks.

In one example, any one of the two types of blocks in a block copolymer—for example, the block 1 and the block 2—may be a crosslinkable block. By applying a crosslinkable block as any one of the blocks, etching selectivity or the like of the block copolymer can be improved. A block can be made into a crosslinkable block by introducing a crosslinking substituent in the block. Examples of a crosslinking functional group may include, but are not limited to, a functional group such as a benzoyl-phenoxy group, an alkenyloxycarbonyl group, a (meth)acryloyl group, an alkenyloxyalkyl group, an azide-containing functional group (e.g. an azide alkylcarbonyloxy group, glycidyl azide, and hydroxyphenyl azide), a sulfur-containing functional group and a functional group that contains an unsaturated double bond that can form a crosslinked structure upon exposure to ultraviolet rays or heat.

The above crosslinking functional group may be contained in each of the aforementioned blocks or introduced into each block as a separate structural unit.

There is no particular limitation to the method of preparing a block copolymer. A block copolymer may be polymerized, for example, by a living radical polymerization (LRP) method, examples of which include synthesis by anionic polymerization in which an organic rare-earth metal complex or organic alkali metal compound is used as the polymerization initiator in the presence of an alkali metal and an inorganic acid salt such as an alkaline earth metal; synthesis by an anionic polymerization method in which an organic alkali metal compound is used as the polymerization initiator in the presence of an organic aluminum compound; an atom transfer radical polymerization (ATRP) method in which an ATRP agent is used as the polymerization-control agent; an activators regenerated by electron transfer (ARGET) ATRP method in which an ATRP agent is used as the polymerization-control agent but the polymerization takes place in the presence of an organic or inorganic reducing agent that generates an electron; an initiators for continuous activator regeneration (ICAR) ATRP method; polymerization by a reversible addition-fragmentation chain transfer (RAFT) for which an inorganic reducing agent and a RAFT agent are used; and a method of using an organic tellurium compound as the initiator, among which a suitable method may be selected for use.

For example, the aforementioned block copolymer may be prepared through polymerization of a reactant (that includes the monomers capable of forming the aforementioned block) by a living radical polymerization method in the presence of a radical initiator and a living radical polymerization reagent. The process of preparing a block copolymer may further include, for example, precipitating, in a nonsolvent, the polymerization product that is produced through the above processes. There is no particular limitation to the type of the radical initiator, and the radical initiator may suitably be selected in consideration of the polymerization efficiency; for example, an azo compound such as azobisisobutyronitrile (AIBN) and 2,2'-azobis-(2,4-dimethylvaleronitrile), or a peroxide series such as benzoyl peroxide (BPO) and di-t-butyl peroxide (DTBP) may be used.

A living radical polymerization process may be carried out, for example, in a solvent such as methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethyl sulfoxide, and dimethylacetamide.

Examples of a nonsolvent include, but are not limited to, an alcohol (such as methanol, ethanol, n-propanol, and isopropanol), a glycol (such as ethylene glycol), n-hexane, cyclohexane, n-heptane, and an ether (such as petroleum ether).

The present application also relates to a polymer film that contains the aforementioned block copolymer. The polymer film may be used in a variety of applications, for example, in a variety of electronic or electrical devices, in the process of forming the aforementioned patterns, in magnetic storage recording media such as flash memory, or in biosensors.

In one example, the aforementioned block copolymer may realize a regular structure, such as a sphere, a cylinder, a gyroid or a lamella, through self-assembly in the aforementioned polymer film. Such a structure may be vertically oriented. For example, the block 1, the block 2 or (in the segment of the other block that is covalently bonded to any of the block 1 and block 2) the segment may form a regular structure such as a lamella form or a cylindrical form in a block copolymer, and such a structure may be vertically oriented.

The above polymer film in the present application may have an in-plane diffraction pattern, which is a peak(s) vertical to the x-component of a GISAXS diffraction pattern, during GISAXS analysis. In another example, the number of the peaks observed along the x-component of the above GISAXS diffraction pattern may be at least 2 and, when there are multiple peaks present, the scattering vector q values of the peaks may be observed to be in an integer ratio.

The present application also relates to a method of forming a polymer film by using the aforementioned block copolymer. The method may include forming a polymer film containing the above block copolymer on a substrate in a self-assembled state. For example, the above method may include depositing the above block copolymer, or a coating solution containing the block copolymer, to form a layer and then annealing the layer. The above annealing process may refer to a thermal annealing process or a solvent annealing process.

The above thermal annealing may be carried out, for example, based on the phase transition temperature or glass transition temperature of the block copolymer; for example, it may be carried out at a temperature equal to or greater than the above glass transition temperature or phase transition temperature. The duration of such thermal annealing is not particularly limited and may be, for example, in the range of about 1 minute to 72 hours, although it may be subject to change as necessary. Also, the heat-treatment temperature during a thermal annealing process may be, for example, about 100° C. to 250° C., which may be subject to change depending on the block copolymer to be used.

In addition, the above solvent annealing process may be carried out in a suitable room-temperature nonpolar solvent and/or polar solvent for about 1 minute to 72 hours.

The present application also relates to a method of forming a pattern. The above method may include, for example, a process of selectively removing the block 1 or block 2 of a block copolymer from the laminate that is made up of a substrate and a polymer film, which is formed on the substrate and contains the above self-assembled block copolymer. The above method may be a method of forming a pattern on the above substrate. For example, the above method may include forming, on a substrate, a polymer film that contains the above block copolymer, selectively removing any one or more blocks of the block copolymer that is present in the above film, and subsequently etching the substrate. The above method enables the formation of a micropattern, for example, in nanoscale. Also, a variety of patterns such as a nanorod and a nanohole may be formed by the above method, depending on the structure of the block copolymer in the polymer film. If needed, the above block copolymer may be mixed with another copolymer, a homopolymer or the like for the formation of patterns. The type of the substrate to be applied in the above method is not particularly limited and may be selected to suit the application; for example, silicon oxide may be used.

For example, the above method may form a silicon oxide-nanoscale pattern that exhibits a high aspect ratio. A variety of forms such as a nanorod and a nanohole may be realized, for example, by forming the above polymer film on the silicon oxide, selectively removing any one block of a block copolymer in the above polymer film where the block copolymer constitutes a predetermined structure, and then etching the silicon oxide by any one of various techniques, for example, by reactive-ion etching. Also, the above method may enable the realization of a nanopattern having a high aspect ratio.

For example, the above pattern may be realized in the scale of tens of nanometers, and such a pattern may be used for a variety of applications including, for example, magnetic recording media for the next-generation information and electronics.

For example, a pattern in which nanostructures (e.g. nanowires) whose width is about 10 nm to 40 nm are arranged spaced apart (e.g. by 20 nm to 80 nm) can be formed by the above method. In another example, a structure in which nanoholes whose width (e.g. diameter) is about 10 nm to 40 nm are arranged spaced apart by about 20 nm to 80 nm can also be realized.

In addition, the nanowires or nanoholes in the above structure can be made to have high aspect ratios.

In the above method, there is no particular limitation to the method of selectively removing any one block of a block copolymer; for example, a method of removing a relatively soft block by having the polymer film irradiated with suitable electromagnetic waves such as ultraviolet rays may be used. In this case, the condition of an ultraviolet ray irradiation is determined by the type of blocks in the block copolymer; for example, it may include an irradiation of the ultraviolet rays whose wavelength is about 254 nm for 1 minute to 60 minutes.

Following the ultraviolet ray irradiation, the process of additionally removing the segment that was previously disintegrated by ultraviolet rays may be carried out by treating the polymer film with an acid or the like.

There is no particular limitation to the process of etching the substrate by using, as the mask, the polymer film that has been selectively removed of certain blocks; for example, the above etching may be carried out through reactive-ion etching with $CF_4/Ar$ ions or the like. The above etching may be followed by the process of removing the polymer film from the substrate through an oxygen plasma treatment or the like.

EFFECT

Figure 1:
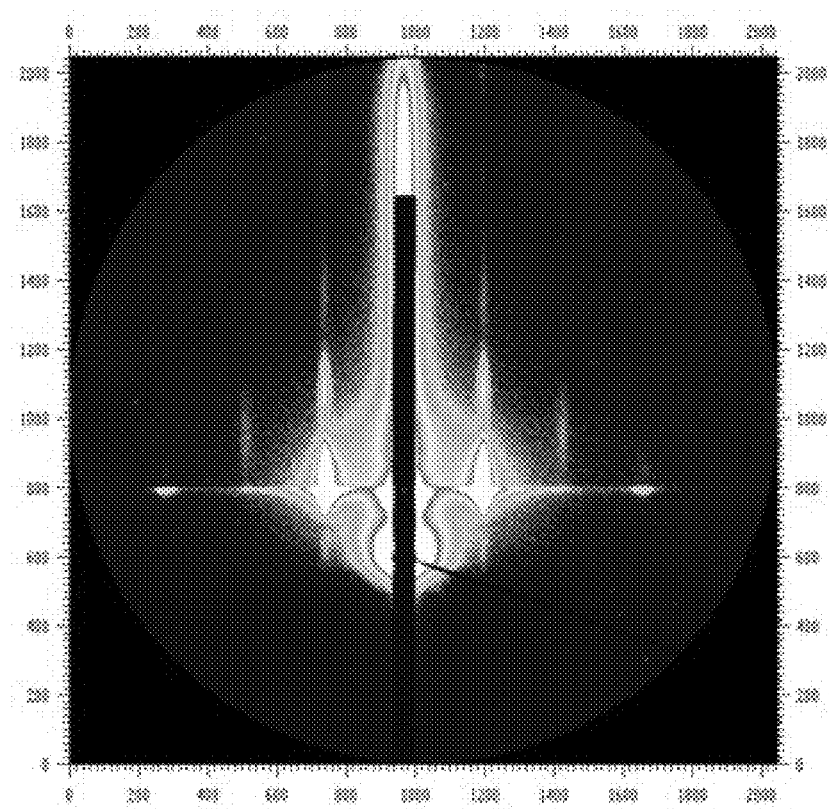
FIGS. 1 and 2 each shows a GISAXS diffraction pattern.

The present application can provide a block copolymer—which exhibits an excellent self-assembling property or phase separation property and, thus, can be used effectively in a variety of applications—and uses thereof.

DETAILED DESCRIPTION OF EMBODIMENTS

The present application is described in more detail hereinafter through examples and comparative examples according to the present application, but the scope of the present application is not limited to the examples which are proposed hereinafter.

1. NMR Measurement

NMR analysis was carried out at room temperature by using a NMR spectrometer that includes a Varian Unity Inova (500 MHz) spectrometer with a 5-mm triple resonance probe. The analysis subject material was diluted with a solvent ($CDCl_3$) for an NMR measurement to a concentration of about 10 mg/ml for use, and the chemical shift was expressed in ppm.

<Applied Abbreviations> br=broad signal, s=singlet, d=doublet, dd=doublet of doublets, t=triplet, dt=doublet of triplets, q=quartet, p=quintet, m=multiplet.

2. Gel Permeation Chromatography (GPC)

The number average molecular weight (Mn) and molecular weight distribution were measured by GPC. The analysis subject material such as a macroinitiator or the block copolymer of the examples or of the comparative examples was put in a 5-mL vial and diluted with tetrahydrofuran (THF) to a concentration of about 1 mg/mL. Then, a standard specimen for calibration and the specimen to be analyzed were filtered with a syringe filter (pore size: 0.45 μm) and subsequently analyzed. ChemStation (Agilent Technologies Inc.) was used as the analytical program, each of the Mw and Mn was obtained by comparing the elution time of the specimen with the calibration curve, and then a molecular weight distribution (polydispersity index, PDI) was calculated as a ratio Mw/Mn. The measuring condition of GPC is as follows:

<GPC Measuring Conditions>

Device: 1200 Series of Agilent Technologies Inc.
Column: Two PLgel MIXED-B of Polymer Laboratories
Solvent: THF
Column temperature: 35° C.
Sample concentration: 1 mg/mL, 200 L is injected
Standard specimen: polystyrene (Mp: 3900000, 723000, 316500, 52200, 31400, 7200, 3940, 485)

3. GISAXS (Grazing-Incidence Small-Angle X-Ray Scattering)

GISAXS analysis was carried out by using a 3C beamline of Pohang accelerator. A coating solution was prepared by dissolving a block copolymer, which is the subject to be analyzed, in fluorobenzene to a solid concentration of about 0.7 wt %, and it was spin-coated on a base material at a thickness of about 5 nm. The coating area was adjusted to about 2.25 $cm^2$ (width: 1.5 cm, length: 1.5 cm). The coated polymer film was dried at room temperature for about 1 hour, and then again thermal-annealed at a temperature of about 160° C. for about 1 hour to induce the formation of a phase-separated structure. Subsequently, a film having a phase-separated structure was formed. After having an X-ray incident on the film at an incident angle of about 0.12 degrees to 0.23 degrees, which is an angle greater than either one of the critical angle of the film and the critical angle of the base material and smaller than the other, an X-ray diffraction pattern that is scattered from the film was obtained by a detector (2D marCCD). In this case, the distance from the film to the detector was set within the range between about 2 m and 3 m in which the self-assembled pattern of the film was well observed. As the base material, a base material that has a hydrophilic surface (a silicon substrate that was treated by piranha solution to have a room-temperature wetting angle of about 5 degrees against purified water) or a base material that has a hydrophobic surface (a silicon substrate that was treated by hexamethyldisilazane (HMDS) to have a room-temperature wetting angle of about 60 degrees against purified water) was used.

4. XRD Analysis Method

XRD analysis was carried out by transmitting X-rays emitted from a 4C beamline of Pohang accelerator through a specimen and measuring the scattering intensity that changes in response to the scattering vector q. A polymer that had been synthesized without being pre-treated in a particular manner was purified, then dried in a vacuum oven for about one day to be formed into a powder, and placed in a cell for XRD measurement to be used as the specimen. For XRD pattern analysis, an X-ray whose vertical size is 0.023 mm and horizontal size is 0.3 mm was used, and a 2D marCCD detector was used. The 2D diffraction pattern that is scattered from the specimen was obtained in the form of an image. The obtained diffraction pattern was analyzed by a numerical analytical method that applies least-squares regression to obtain information such as the scattering vector and FWHM. An Origin program was used for the above analysis, and the part that corresponds to the minimum intensity in an XRD diffraction pattern was set as the baseline and the minimum intensity was set as zero, then the peak profile of the above XRD pattern was subject to Gaussian fitting, and the aforementioned scattering vector and FWHM were obtained from the fitted result. When the above Gaussian fitting was performed, the R-square value was set to be at least 0.96.

5. Surface Energy Measurement

A surface energy may be measured by using the Drop Shape Analyzer DSA100 (manufactured by KRUSS GmbH). The material (i.e. a polymer) to be measured was dissolved in fluorobenzene to a solid concentration of about 2 wt % to prepare a coating solution, which was spin-coated on a substrate at a thickness of about 50 nm and a coating area of 4 $cm^2$ (width: 2 cm, length: 2 cm). The coated layer was dried at room temperature for about 1 hour and then thermal-annealed at 160° C. for about 1 hour. The process of measuring a contact angle by dropping deionized water, whose surface tension is well known in the art, on the above thermal-annealed film was repeated for 5 times, and the 5 measured values of a contact angle were averaged. Similarly, the process of measuring a contact angle by dropping diiodomethane, whose surface tension is well-known in the art, on the above thermal-annealed film was repeated for 5 times, and the 5 measured values of a contact angle were averaged. Subsequently, the surface energies were obtained by using the averaged values of the contact angle, which were measured respectively with deionized water and diiodomethane, and substituting the numerical value (Strom value) that corresponds to the surface tension of a solvent into the equations according to the Owens-Wendt-Rabel-Kaelble method. The numerical value that corresponds to the surface energy of each block of a block copolymer was obtained by using the above-described method on a homopolymer that was made up of only the monomers that constitute the above block.

6. GIWAXS (Grazing-Incidence Wide-Angle X-Ray Scattering)

GIWAXS analysis was carried out by using a 3C beamline of Pohang accelerator. A coating solution was prepared by dissolving a block copolymer, which is the subject to be analyzed, in toluene to a solid concentration of about 1 wt %, and it was spin-coated on a base material at a thickness of about 30 nm. The coating area was adjusted to about 2.25 $cm^2$ (width: 1.5 cm, length: 1.5 cm). The coated polymer film was dried at room temperature for about 1 hour, and then again thermal-annealed at a temperature of about 160° C. for about 1 hour to form a film. After having an X-ray incident on the film at an incident angle of about 0.12 degrees to 0.23 degrees, which is an angle greater than either one of the critical angle of the film and the critical angle of the base material and smaller than the other, an X-ray diffraction pattern that is scattered from the film was obtained by a detector (2D marCCD). In this case, the distance from the film to the detector was set within the range between about 0.1 m and 0.5 m in which the crystalline or liquid-crystalline structure of the film was well observed. A silicon substrate that was treated by piranha solution to have a room-temperature wetting angle of about 5 degrees against purified water was used as the base material.

The scattering intensity in the azimuthal angle (i.e. the azimuthal angle when an angle measured in the upward direction of the diffraction pattern (i.e. the angle of out-of-plane diffraction pattern) is set as 0 degrees) range of −90 degrees to 90 degrees in a diffraction pattern of a GIWAXS spectrum—where the scattering vector ranged from 12 $nm^{-1}$ to 16 $nm^{-1}$—was plotted as a graph, and the FWHM was measured through Gaussian fitting of the graph. In the case where only a half of a peak was observed from Gaussian fitting, the twice the FWHM value of the obtained (observed) peak was defined as the FWHM of the peak.

7. DSC Analysis

DSC analysis was carried out by using DSC800 (PerkinElmer Inc). An endothermic curve was obtained by a method that applies the above apparatus, in which the subject specimen to be analyzed was heated under a nitrogen atmosphere at a rate of 10° C. per minute from 25° C. to 200° C., cooled at a rate of −10° C. per minute from 200° C. to −80° C., and then again heated at a rate of 10° C. per minute from −80° C. to 200° C. The obtained endothermic curve was analyzed to estimate the temperature (i.e. melting transition temperature, Tm) at which a melting transition peak appears, the temperature (i.e. isotropic transition temperature, Ti) at which an isotropic transition peak appears, and the area of each peak. Here, each of the above temperatures was determined by the temperature that corresponds to the summit of each peak. The area per unit mass of each peak can be determined by dividing the peak area by the mass of the specimen, and such a calculation is possible through a program that is provided by the DSC apparatus.

8. Measurement of X by Equation A

Each of the variables of Mathematical Expression A-D, M, K and L—can be obtained as follows:

First of all, D can be obtained by putting a specimen to be analyzed (i.e. a homopolymer that is prepared with only the monomer that constitutes the block 1 or a homopolymer that is prepared with only the monomer that constitutes the block 2) in a solvent (i.e. ethanol) whose mass and density in air are known, obtaining the density of each block through the mass of the specimen, and calculating the ratio of the masses of different types of specimen.

Also, M can be obtained as the ratio of molar masses of monomers that make up blocks in a block copolymer. For example, in the case of each block copolymer of an example, the molar mass of the monomer of Preparation Example 1, which is the monomer that constitutes the block 1 that will be described below in the present specification, is 346.5 g/mol, the molar mass of pentafluorostyrene that constitutes the block 2 is 194.1 g/mol, and, from the ratio, the value of M can be calculated to be about 1.79.

In addition, L can be obtained as the ratio of number of hydrogen atoms in the monomers that make up blocks in a block copolymer. For example, in the case of each block copolymer of an example, the number of hydrogen atoms in the monomer of Preparation Example 1, which is the monomer that constitutes the block 1, is 34, the number of hydrogen atoms in pentafluorostyrene that constitutes the block 2 is 3, and, from the ratio, the value of L can be calculated to be about 11.3.

Lastly, K can be calculated through the area of a spectrum that is obtained by the aforementioned NMR analysis method. In this case, when the peaks—each of which is obtained from each block in a block copolymer—do not overlap each other, the area of the peak derived from each block is simply analyzed, and K can be obtained as the ratio of the peak areas.

Figure 18:
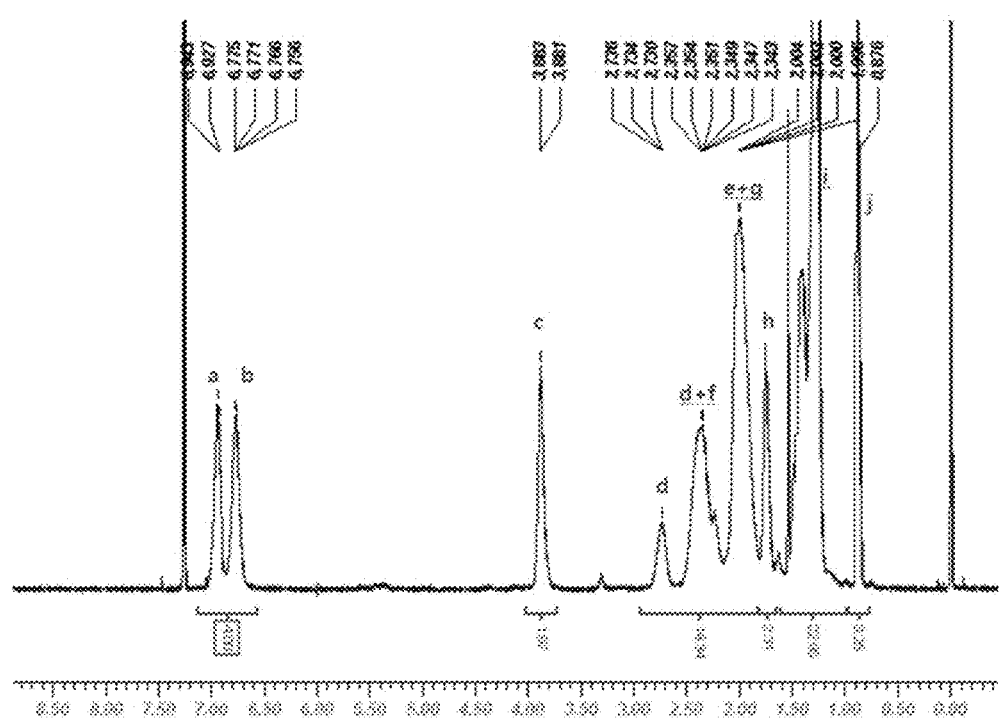
FIG. 18 exemplifies a method of calculating the value of K in Mathematical Expression A.

In contrast, when the peaks derived from different blocks of a block copolymer overlap each other at least partly, the overlapped part should be taken into consideration when obtaining the value of K. For example, the accompanying FIG. 18 is an illustrative NMR spectrum of a block copolymer that contains a structural unit, which is derived from the compound represented by Structural Formula A that is prepared according to Preparation Example 1 and applied in the following examples and comparative examples, and a structural unit derived from pentafluorostyrene. In FIG. 18, the part that is marked as e and the part that is marked as d refer to the peaks that come from the block 2 (that is, the aforementioned structural unit that is derived from pentafluorostyrene), and the rest (a, b, c, f, g, h, i and j) are the peaks that come from a structural unit that is derived from the compound (represented by Structural Formula A) of Preparation Example 1. As can be seen in the graph, the peaks marked as e and g and the peaks marked as d and f overlap each other; in which case, the overlapping of the peaks should be taken into consideration when obtaining the value of K.

In this case, the method of obtaining the value of K by taking the overlapping of the peaks into account is well known in the art; the value can be obtained, for example, by using an NMR interpretation program such as a MestReC program.

Preparation Example 1. Synthesis of Monomer A

The compound DPM-C12 represented by the following Structural Formula A was synthesized by the following method: hydroquinone (10.0 g, 94.2 mmol) and 1-bromododecane (23.5 g, 94.2 mmol) were introduced into a 250-mL flask, dissolved in 100 mL of acetonitrile; then, an excessive amount of potassium carbonate was added to the above solution and allowed to react at about 75° C. for about 48 hours under a nitrogen atmosphere; upon completion of the reaction, the reaction products were filtered to be removed of the remaining potassium carbonate and acetonitrile that was used for the reaction; then the substances were worked up through an addition of a mixed solvent of dichloromethane (DCM) and water, and the separated organic layer was collected and dehydrated with MgSO$_4$; subsequently, the substances were purified by column chromatography (CC) with DCM to obtain a white solid target material (i.e. 4-(dodecyloxy)-phenol with a yield of about 37%.

<NMR Analysis Results>
$^1$H-NMR (CDCl$_3$): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

The synthesized 4-(dodecyloxy)-phenol (9.8 g, 35.2 mmol), methacrylic acid (6.0 g, 69.7 mmol), dicyclohexylcarbodiimide (DCC) (10.8 g, 52.3 mmol) and p-dimethylaminopyridine (DMAP) (1.7 g, 13.9 mmol) were introduced into a flask, 120 mL of methylene chloride was added, and then allowed to react at room temperature for 24 hours under a nitrogen atmosphere; upon completion of the reaction, the reaction products were filtered to be removed of a urea salt that was produced during the reaction and also of the remaining methylene chloride; then, the substances were removed of impurities by column chromatography (CC) that uses hexane and dichloromethane (DCM) as the mobile phase, the obtained products were recrystallized in a mixed solvent of methanol and water (mixed in a weight ratio of 1:1) to obtain a white solid target material (7.7 g, 22.2 mmol) with a yield of 63%.

<NMR Analysis Results>
$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

[Structural Formula A]

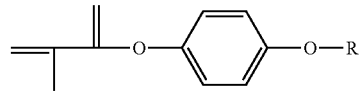

In Structural Formula A, R represents a linear-chain alkyl group with 12 carbons.

Preparation Example 2. Synthesis of Monomer G

The compound represented by the following Structural Formula G was synthesized by the method of Preparation Example 1, except that 1-bromobutane was used instead of 1-bromododecane. The results of NMR analysis on the above compound are as follows.

<NMR Analysis Results>
$^1$H-NMR (CDCl$_3$): δ7.02 (dd, 2H); δ6.89 (dd, 2H); δ6.33 (dt, 1H); δ5.73 (dt, 1H); δ3.95 (t, 2H); δ2.06 (dd, 3H); δ1.76 (p, 2H); δ1.49 (p, 2H); δ0.98 (t, 3H).

[Structural Formula G]

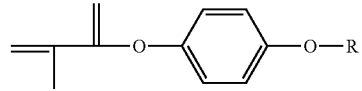

In Structural Formula G, R represents a linear-chain alkyl group with 4 carbons.

Preparation Example 3. Synthesis of Monomer B

The compound represented by the following Structural Formula B was synthesized by the method of Preparation Example 1, except that 1-bromooctane was used instead of 1-bromododecane. The results of NMR analysis on the above compound are as follows.

<NMR Analysis Results>
$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.45 (p, 2H); 1.33-1.29 (m, 8H); δ0.89 (t, 3H).

[Structural Formula B]

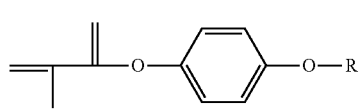

In Structural Formula B, R represents a linear-chain alkyl group with 8 carbons.

Preparation Example 4. Synthesis of Monomer C

The compound represented by the following Structural Formula C was synthesized by the method of Preparation Example 1, except that 1-bromodecane was used instead of 1-bromododecane. The results of NMR analysis on the above compound are as follows.
<NMR Analysis Results>
$^1$H-NMR (CDCl$_3$): δ7.02 (dd, 2H); δ6.89 (dd, 2H); δ6.33 (dt, 1H); δ5.72 (dt, 1H); δ3.94 (t, 2H); δ2.06 (dd, 3H); δ1.77 (p, 2H); δ1.45 (p, 2H); 1.34-1.28 (m, 12H); δ0.89 (t, 3H).

[Structural Formula C]

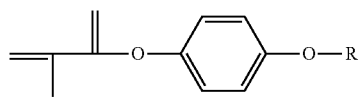

In Structural Formula C, R represents a linear-chain alkyl group with 10 carbons.

Preparation Example 5. Synthesis of Monomer D

The compound represented by the following Structural Formula D was synthesized by the method of Preparation Example 1, except that 1-bromotetradecane was used instead of 1-bromododecane. The results of NMR analysis on the above compound are as follows.
<NMR Analysis Results>
$^1$H-NMR (CDCl$_3$): δ7.02 (dd, 2H); δ6.89 (dd, 2H); δ6.33 (dt, 1H); δ5.73 (dt, 1H); δ3.94 (t, 2H); δ2.05 (dd, 3H); δ1.77 (p, 2H); δ1.45 (p, 2H); 1.36-1.27 (m, 20H); δ0.88 (t, 3H.)

[Structural Formula D]

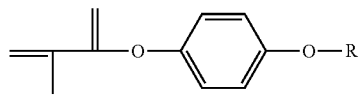

In Structural Formula D, R represents a linear-chain alkyl group with 14 carbons.

Preparation Example 6. Synthesis of Monomer E

The compound represented by the following Structural Formula E was synthesized by the method of Preparation Example 1, except that 1-bromohexadecane was used instead of 1-bromododecane. The results of NMR analysis on the above compound are as follows.
<NMR Analysis Results>
$^1$H-NMR (CDCl$_3$): δ7.01 (dd, 2H); δ6.88 (dd, 2H); δ6.32 (dt, 1H); δ5.73 (dt, 1H); δ3.94 (t, 2H); δ2.05 (dd, 3H); δ1.77 (p, 2H); δ1.45 (p, 2H); 1.36-1.26 (m, 24H); δ0.89 (t, 3H)

[Structural Formula E]

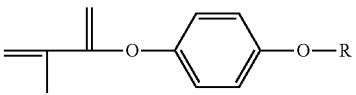

In Structural Formula E, R represents a linear-chain alkyl group with 16 carbons.

Results of GIWAXS and DSC Analyses 6 types of homopolymers were prepared by using the monomers each of which was prepared according to one of Preparation Examples 1 to 6, and the analyzed results of GIWAXS and DSC on each homopolymer are summarized and provided in the following Table 1. Here, the homopolymers were prepared by the method of using each type of monomer to synthesize a macroinitiator according to the following examples or comparative examples. The results of GIWAXS analyses of the preparation examples are provided in FIGS. 12 to 17. Each of FIGS. 12 to 17 corresponds respectively to an image that shows the result of GIWAXS analysis of each of Preparation Examples 1 to 6.

Figure 12:
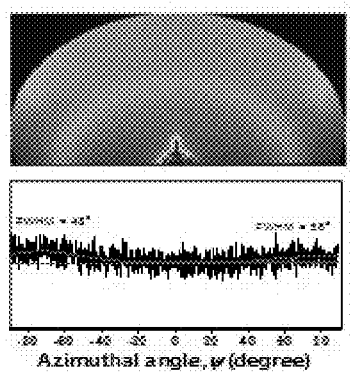
FIGS. 12 to 17 each shows the results of GIWAXS analysis.
Figure 13:
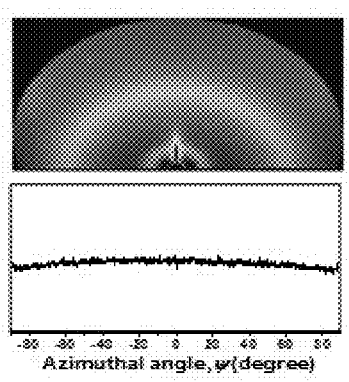
Figure 14:
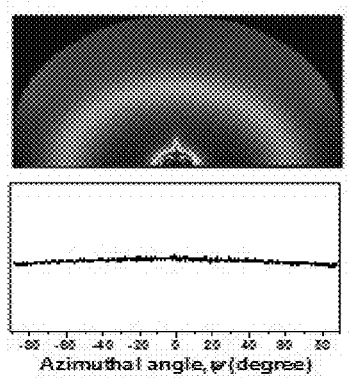
Figure 15:
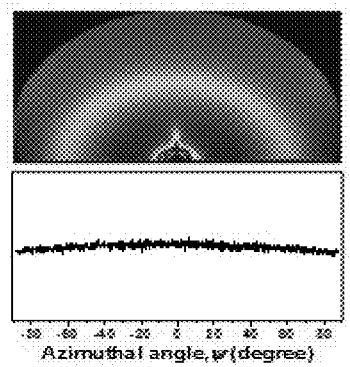
Figure 16:
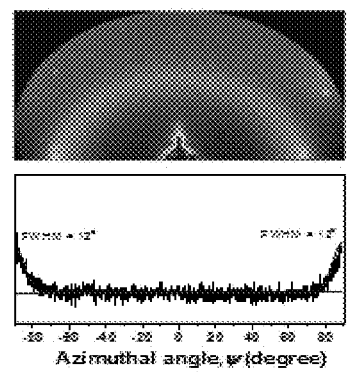
Figure 17:
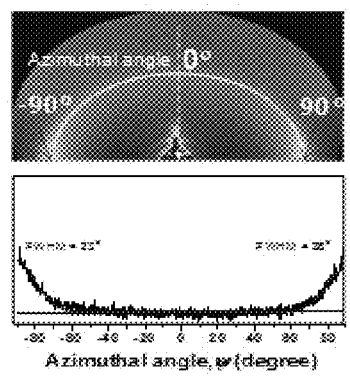

In FIG. 12, the R-square of Gaussian fitting was about 0.264, in FIG. 16, the R-square was about 0.676, and in FIG. 17, the R-square was about 0.932.

TABLE 1

|  | Preparation Examples | | | | | |
|---|---|---|---|---|---|---|
|  | 1 | 2 | 3 | 4 | 5 | 6 |
| Tg | — | 33 | 29 | — | — | — |
| Tm | −3 | — | — | — | 23 | 46 |
| Ti | 15 | — | — | 44 | 60 | 60 |
| M/I | 3.67 | — | — | — | 5.75 | 71.86 |
| FWHM1 | 48 | — | — | — | 13 | 23 |
| FWHM2 | 58 | — | — | — | 12 | 26 |
| Chain-forming atoms | 12 | 4 | 8 | 10 | 14 | 16 |

Tg: Glass transition temperature (Unit: ° C.)
Tm: Melting transition temperature (Unit: ° C.)
Ti: Isotropic transition temperature (Unit: ° C.)
M/I: Ratio of melting transition peak area (M) to isotropic transition peak area (I)
FWHM1: FWHM of peak at azimuthal angle range of −90 degrees to −70 degrees in GIWAXS diffraction pattern, where scattering vector ranges from 12 nm$^{-1}$ to 16 nm$^{-1}$ (Unit: degrees)
FWHM2: FWHM of peak at azimuthal angle range of 70 degrees to 90 degrees in GIWAXS diffraction pattern, where scattering vector ranges from 12 nm$^{-1}$ to 16 nm$^{-1}$ (Unit: degrees)
Chain-forming atoms: number of chain-forming atoms in block1 (= number of carbon atoms in R of structural formula of each preparation example)

Example 1

Figure 2:
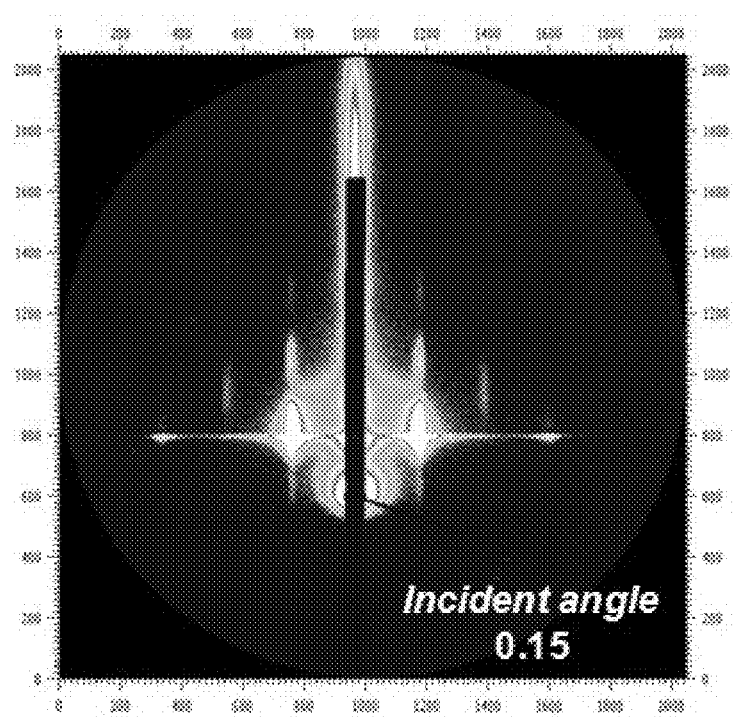
Figure 3:
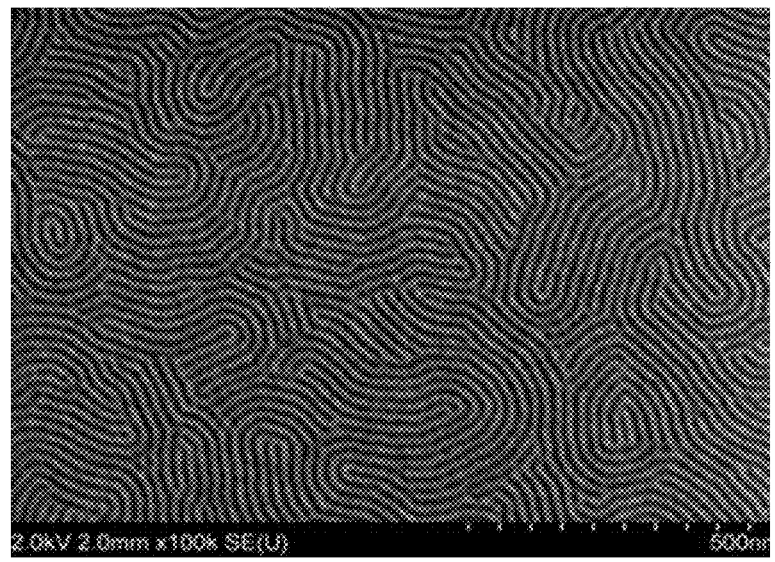
FIGS. 3 to 11 each shows a SEM image of a polymer film.
Figure 4:
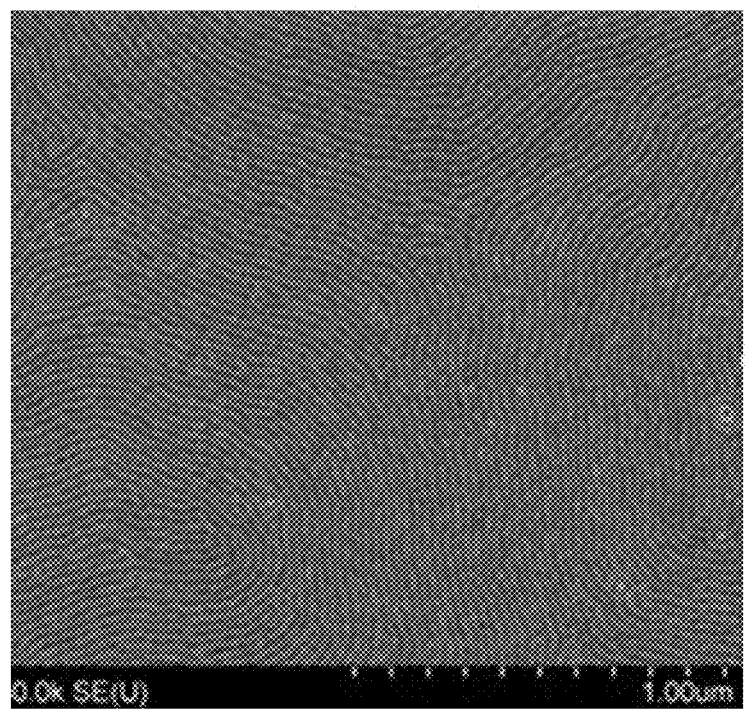
Figure 5:
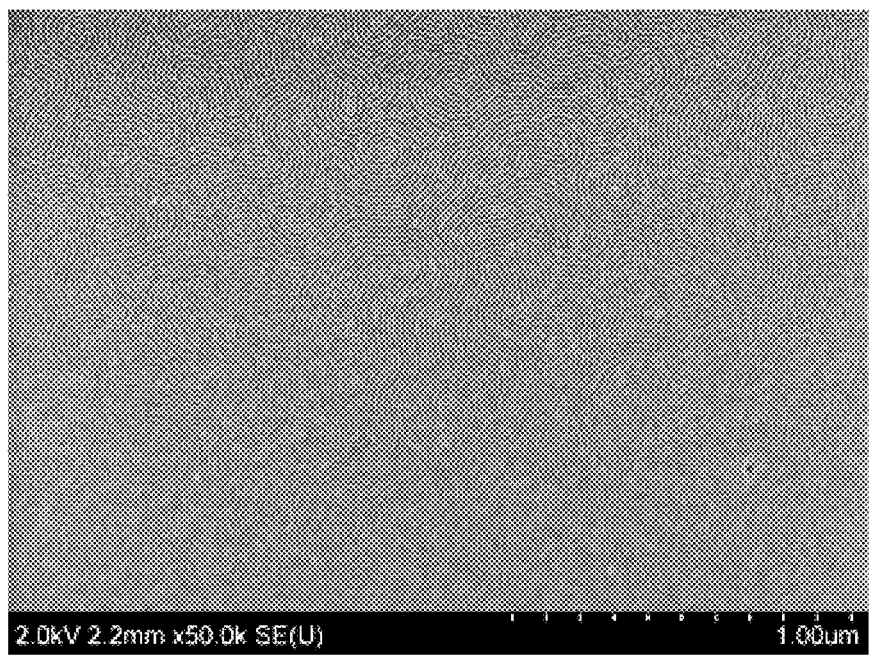
Figure 6:
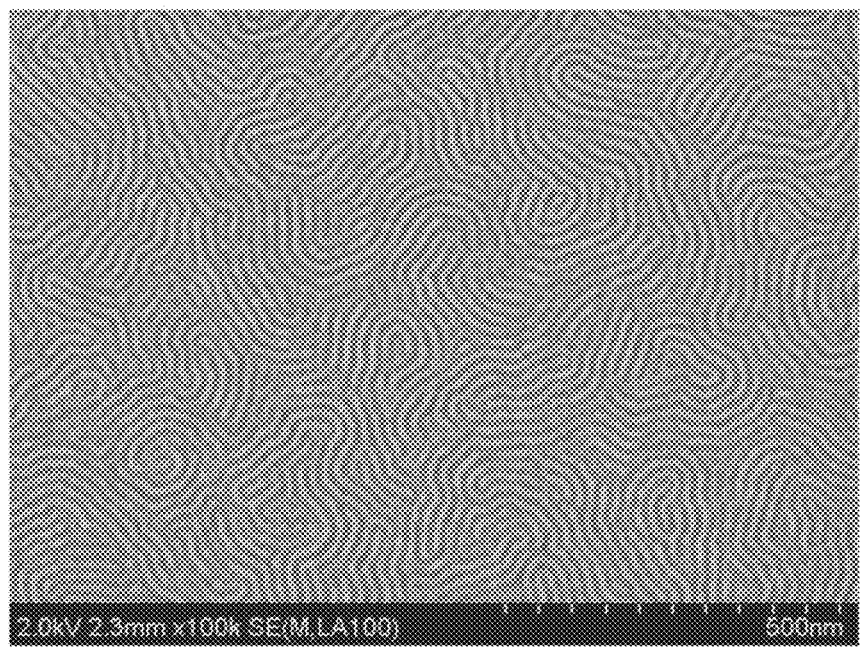
Figure 7:
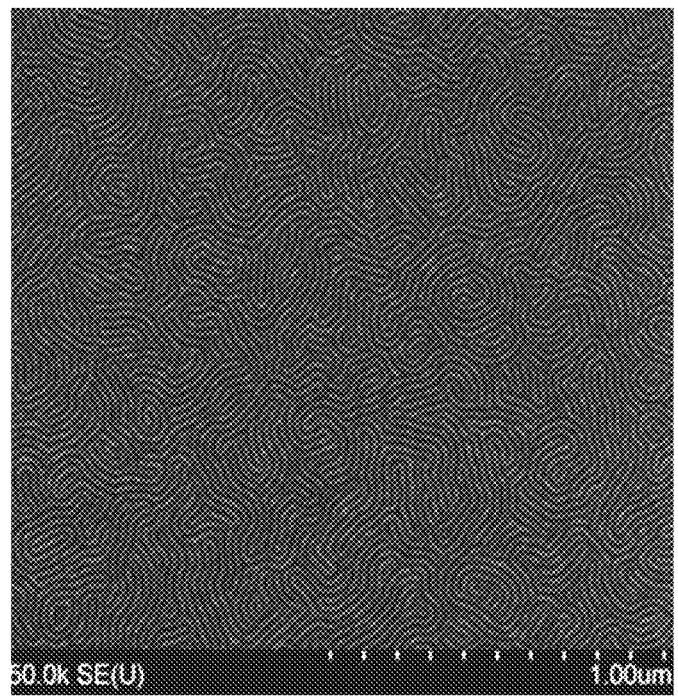

1.785 g of monomer A of Preparation Example 1, 38 mg of a Reversible Addition-Fragmentation chain Transfer (RAFT) reagent (cyanoisopropyl dithiobenzoate), 14 mg of a radical initiator (azobisisobutyronitrile, AIBN) and 4.765 mL of benzene were introduced into a 10-mL Schlenk flask, stirred at room temperature for 30 minutes under a nitrogen atmosphere, and then a RAFT polymerization reaction was carried out at 70° C. for 4 hours. Upon completion of polymerization, the reaction solution was precipitated in 250 mL of an extraction solvent (methanol) and then dried by filtration under reduced pressure to prepare a pink macroinitiator. The yield of the macroinitiator was about 83.1 wt %, and the number average molecular weight (Mn) and molecular weight distribution (Mw/Mn) were 11,400 and 1.15, respectively. 0.3086 g of the macroinitiator, 1.839 g of a pentafluorostyrene monomer and 0.701 mL of benzene were introduced into a 10-mL Schlenk flask, stirred at room temperature for 30 minutes under a nitrogen atmosphere, and then a RAFT polymerization reaction was carried out at 115° C. for 4 hours. Upon completion of polymerization, the reaction solution was precipitated in 250 mL of an extraction solvent (methanol) and then dried by filtration under reduced pressure to prepare a light-pink block copolymer. The yield of the block copolymer was about 27.1 wt %, and the Mn and Mw/Mn were 18,900 and 1.19, respectively. The above block copolymer contains the block 1 (that is derived from monomer A prepared according to Preparation Example 1) and the block 2 (that is derived from the aforementioned pentafluorostyrene monomer). The results of GISAXS measurement that was performed, in the aforementioned manner, on a hydrophilic surface (the surface whose room-temperature wetting angle against purified water is 5 degrees) of the block copolymer are provided in FIG. 1, and the results of GISAXS measurement on a hydrophobic surface (the surface whose room-temperature wetting angle against purified water is 60 degrees) are provided in FIG. 2. It is indicated in FIGS. 1 and 2 that an in-plane diffraction pattern was produced from GISAXS in any case.

Example 2

A block copolymer was prepared according to the method of Example 1 by using the macroinitiator and pentafluorostyrene as the monomers, except that monomer B from Preparation Example 3 was used instead of monomer A from Preparation Example 1. The block copolymer contains the block 1 (that is derived from monomer B of Preparation Example 3) and the block 2 (that is derived from the aforementioned pentafluorostyrene monomer). GISAXS was conducted on the block copolymer by the method described in Example 1, and an in-plane diffraction pattern was observed on both the hydrophilic surface and the hydrophobic surface.

Example 3

A block copolymer was prepared according to the method of Example 1 by using the macroinitiator and pentafluorostyrene as the monomers, except that monomer C from Preparation Example 4 was used instead of monomer A from Preparation Example 1. The block copolymer contains the block 1 (that is derived from monomer C of Preparation Example 4) and the block 2 (that is derived from the aforementioned pentafluorostyrene monomer). GISAXS was conducted on the block copolymer by the method described in Example 1, and an in-plane diffraction pattern was observed on both the hydrophilic surface and the hydrophobic surface.

Example 4

A block copolymer was prepared according to the method of Example 1 by using the macroinitiator and pentafluorostyrene as the monomers, except that monomer D from Preparation Example 5 was used instead of monomer A from Preparation Example 1. The block copolymer contains the block 1 (that is derived from monomer D of Preparation Example 5) and the block 2 (that is derived from the aforementioned pentafluorostyrene monomer). GISAXS was conducted on the block copolymer by the method described in Example 1, and an in-plane diffraction pattern was observed on both the hydrophilic surface and the hydrophobic surface.

Example 5

A block copolymer was prepared according to the method of Example 1 by using the macroinitiator and pentafluorostyrene as the monomers, except that monomer E from Preparation Example 6 was used instead of monomer A from Preparation Example 1. The block copolymer contains the block 1 (that is derived from monomer E of Preparation Example 6) and the block 2 (that is derived from the aforementioned pentafluorostyrene monomer). GISAXS was conducted on the block copolymer by the method described in Example 1, and an in-plane diffraction pattern was observed on both the hydrophilic surface and the hydrophobic surface.

Comparative Example 1

A block copolymer was prepared according to the method of Example 1 by using the macroinitiator and pentafluorostyrene as the monomers, except that monomer G from Preparation Example 2 was used instead of monomer A from Preparation Example 1. The block copolymer contains the block 1 (that is derived from monomer G of Preparation Example 2) and the block 2 (that is derived from the aforementioned pentafluorostyrene monomer). GISAXS was conducted on the block copolymer by the method described in Example 1, but an in-plane diffraction pattern was not observed on any of the hydrophilic surface and the hydrophobic surface.

Comparative Example 2

A block copolymer was prepared according to the method of Example 1 by using the macroinitiator and pentafluorostyrene as the monomers, except that 4-methoxyphenyl methacrylate was used instead of monomer A from Preparation Example 1. The block copolymer contains the block 1 (that is derived from 4-methoxyphenyl methacrylate) and the block 2 (that is derived from the aforementioned pentafluorostyrene monomer). GISAXS was conducted on the block copolymer by the method described in Example 1, but an in-plane diffraction pattern was not observed on any of the hydrophilic surface and the hydrophobic surface.

Comparative Example 3

A block copolymer was prepared according to the method of Example 1 by using the macroinitiator and pentafluorostyrene as the monomers, except that dodecyl methacrylate was used instead of monomer A from Preparation Example 1. The block copolymer contains the block 1 (that is derived from dodecyl methacrylate) and the block 2 (that is derived from the aforementioned pentafluorostyrene monomer). GISAXS was conducted on the block copolymer by the method described in Example 1, but an in-plane diffraction pattern was not observed on any of the hydrophilic surface and the hydrophobic surface.

The results of GPC measurement on the macroinitiators and prepared block copolymers of the above examples and comparative examples are summarized and provided in the following Table 2.

TABLE 2

|     |     | Examples | | | | | Comparative Examples | | |
| --- | --- | --- | --- | --- | --- | --- | --- | --- | --- |
|     |     | 1 | 2 | 3 | 4 | 5 | 1 | 2 | 3 |
| MI  | Mn  | 11400 | 9300 | 8500 | 8700 | 9400 | 9000 | 7800 | 8000 |
|     | PDI | 1.15 | 1.16 | 1.14 | 1.18 | 1.15 | 1.17 | 1.13 | 1.16 |
| BCP | Mn  | 18900 | 19900 | 17100 | 17400 | 18900 | 18800 | 18700 | 16700 |
|     | PDI | 1.19 | 1.18 | 1.17 | 1.18 | 1.17 | 1.20 | 1.16 | 1.20 |

MI: Macroinitiator
BCP: Block copolymer
Mn: Number average molecular weight
PDI: Molecular weight distribution The properties of the block copolymers prepared as the above were evaluated in the aforementioned manner, and the results are summarized and provided in the following Table 3.

TABLE 3

|     |     | Examples | | | | | Comparative Examples | | | Ref |
| --- | --- | --- | --- | --- | --- | --- | --- | --- | --- | --- |
|     |     | 1 | 2 | 3 | 4 | 5 | 1 | 2 | 3 |     |
| Block 1 | SE | 30.83 | 31.46 | 27.38 | 26.924 | 27.79 | 37.37 | 48.95 | 19.1 | 38.3 |
|     | De | 1 | 1.04 | 1.02 | 0.99 | 1.00 | 1.11 | 1.19 | 0.93 | 1.05 |
| Block 2 | SE | 24.4 | 24.4 | 24.4 | 24.4 | 24.4 | 24.4 | 24.4 | 24.4 | 41.8 |
|     | De | 1.57 | 1.57 | 1.57 | 1.57 | 1.57 | 1.57 | 1.57 | 1.57 | 1.18 |
| Difference in SE | | 6.43 | 7.06 | 2.98 | 2.524 | 3.39 | 12.98 | 24.55 | 5.3 | 3.5 |
| Difference in De | | 0.57 | 0.53 | 0.55 | 0.58 | 0.57 | 0.46 | 0.38 | 0.64 | 0.13 |
| Chain-forming atoms | | 12 | 8 | 10 | 14 | 16 | 4 | 1 | 12 | — |
| n/D | | 3.75 | 3.08 | 3.45 | 4.24 | 4.44 | 2.82 | 1.98 | — | — |

SE: Surface energy (Unit: mN/m)
De: Density (Unit: g/cm$^3$)
Difference in SE: Absolute value of difference in surface energies of block 1 and block 2
Difference in De: Absolute value of difference in densities of block 1 and block 2
Chain-forming atoms: number of chain-forming atoms in block 1
n/D: numerical value calculated by Equation 1 (nq/(2 × π)) (n: number of chain-forming atoms, q represents numerical value of scattering vector at which peak with largest peak area is observed in scattering vector range of 0.5 nm$^{-1}$ to 10 nm$^{-1}$)
Ref: polystyrene-poly(methyl methacrylate) block copolymer (block 1: polystyrene block, block 2: poly(methyl methacrylate) block The analyzed results of XRD pattern of the macroinitiator (i.e. the block 1) that was used in the preparation of each of the above block copolymers are summarized and provided in the following Table 4 (in the case of Comparative Example 3, not a single peak was observed in the scattering vector range of 0.5 nm$^{-1}$ to 10 nm$^{-1}$).

TABLE 4

|     | Examples | | | | | Comparative | | |
| --- | --- | --- | --- | --- | --- | --- | --- | --- |
|     | 1 | 2 | 3 | 4 | 5 | 1 | 2 | 3 |
| Value of q peak (Unit: nm$^{-1}$) | 1.96 | 2.41 | 2.15 | 1.83 | 1.72 | 4.42 | 3.18 | — |
| FWHM (Unit: nm$^{-1}$) | 0.57 | 0.72 | 0.63 | 0.45 | 0.53 | 0.97 | 1.06 | — |

Test Example 1. Evaluation of Self-Assembling Property

Figure 8:
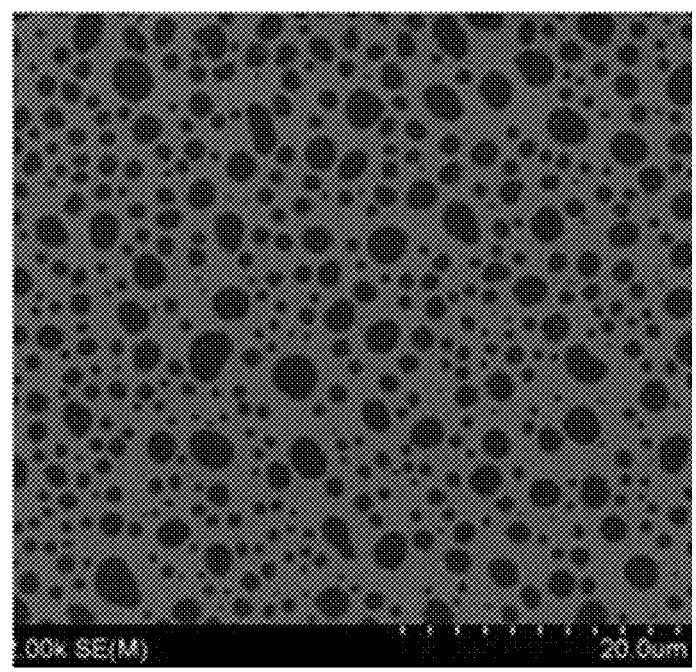

The coating solution prepared by dissolving the block copolymer of an example or comparative example in fluorobenzene to a solid concentration of 0.7 wt % was spin-coated (coating area: width×length=1.5 cm×1.5 cm) on a silicon wafer to a thickness of about 5 nm, dried at room temperature for about 1 hour, and then thermal-annealed at a temperature of about 160° C. for about 1 hour to form a self-assembled film. A scanning electron microscopic (SEM) image was taken of the film. Each of FIGS. 3 to 7 corresponds respectively to a SEM image of each film of Examples 1 to 5. As indicated in the images, each of the block copolymers of examples had a self-assembled film that was effectively formed in a line pattern. In contrast, in the case of comparative examples, the phase separation was not induced at a sufficient level. For example, FIG. 8 shows the result of SEM of Comparative Example 3, which indicates that the phase separation was not effectively induced.

Test Example 2. Evaluation of Self-Assembling Property

Figure 9:
Figure 10:
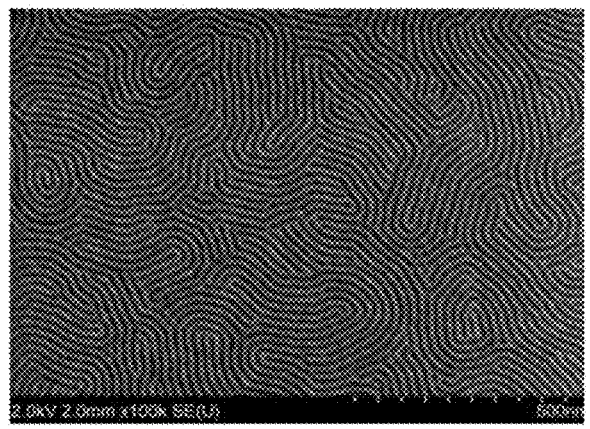
Figure 11:
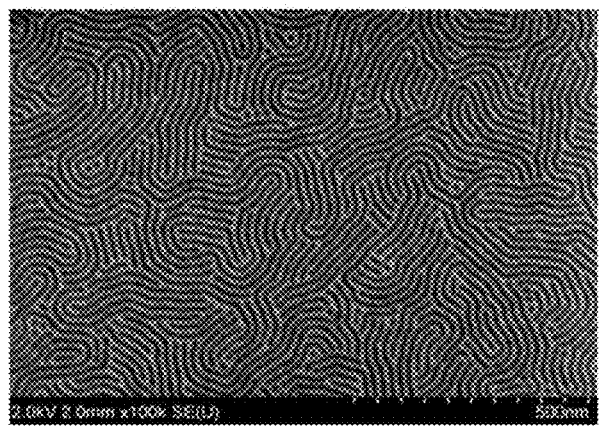

A polymer film was formed, by the method described in Test Example 1 on the block copolymer that had been prepared in Example 1. Each polymer film was formed on each of a silicon substrate which had been treated with piranha solution to have a room-temperature wetting angle of 5 degrees against purified water, a silicon oxide substrate in which the above wetting angle is about 45 degrees, and a HMDS-treated silicon substrate in which the above wetting angle is about 60 degrees. FIGS. 9 to 11 show SEM images of polymer films having the above wetting angle of 5 degrees, 45 degrees and 60 degrees, respectively. The images indicate that the block copolymers are capable of effectively realizing phase-separated structures, regardless of the surface property of the substrate.

Test Example 3

Block copolymers BCP1 to BCP4 were prepared by the method described in Example 1, except that the values of X in Mathematical Expression A were adjusted by controlling the molar ratio between monomers and macroinitiators, or the like.

TABLE 3

| | Values of X in Mathematical Expression A | D | M | K | L |
|---|---|---|---|---|---|
| BCP1 | 2.18 | 1.57 | 1.79 | 0.21 | 11.3 |
| BCP2 | 1.85 | 1.57 | 1.79 | 0.29 | 11.3 |
| BCP3 | 1.75 | 1.57 | 1.79 | 0.33 | 11.3 |
| BCP4 | 1.26 | 1.57 | 1.79 | 0.95 | 11.3 |

D: Ratio D2/D1 of density D2 of block 2 to density D1 of block 1
M: Ratio M1/M2 of molar mass (346.5 g/mol, M1) of monomer of Structural Formula A from Preparation Example 1 (which is monomer that constitutes block 1) to molar mass (194.1 g/mol, M2) of pentafluorostyrene (which is monomer that constitutes block 2)
K: Ratio A2/A1 of area A2 of peak that is obtained, during $^1$H-NMR, based on block 2 to area A1 of peak that is based on block 1
L: Ratio H1/H2 of number (34, H1) of hydrogen atoms in monomer of Structural Formula A from Preparation Example 1 (which is monomer that constitutes block 1) to number (3, H2) of hydrogen atoms in pentafluorostyrene (which is monomer that constitutes block 2)

Figure 19:
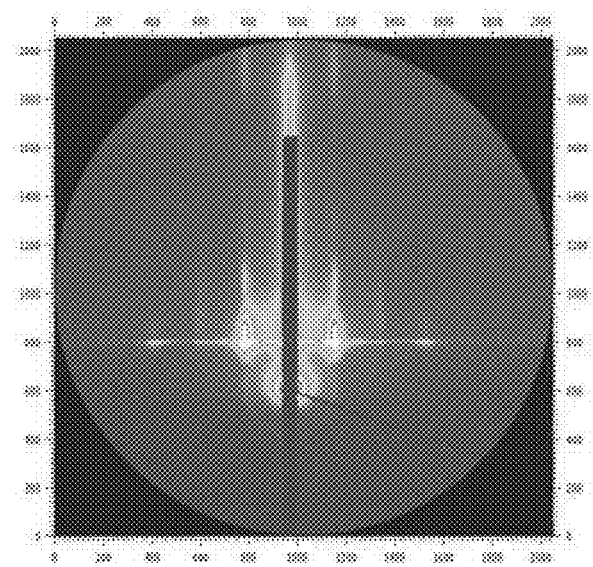
FIGS. 19 to 21 each shows a GISAXS diffraction pattern.
Figure 20:
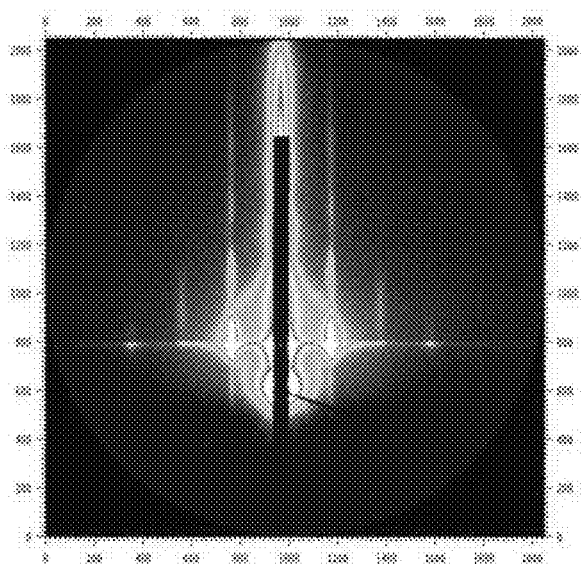
Figure 21:
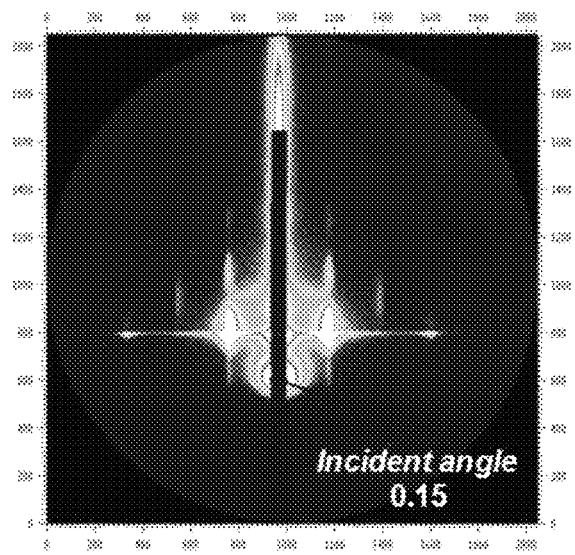

The coating solution prepared by dissolving each of the above block copolymers in fluorobenzene to a solid concentration of 0.7 wt % was spin-coated (coating area: width×length=1.5 cm×1.5 cm) on a silicon wafer to a thickness of about 5 nm, dried at room temperature for about 1 hour, and then thermal-annealed at a temperature of about 160° C. for about 1 hour to form a film. GISAXS was performed on the above film, and the measured results were produced as images. FIGS. 19 to 21 show the results on BCP1, BCP2 and BCP3, respectively. It is indicated in the images that GISAXS in-plane diffraction patterns were observed in the above block copolymer. However, in the case of BCP4, any clear result was not identified.

What is claimed is:

1. A block copolymer comprising a first block and a second block, wherein the first block satisfies one or more of Conditions 1 to 4 below, and the first block and the second block have different chemical structures from each other and an absolute value of a difference in surface energies of 10 mN/m or less, wherein, Condition 1: A peak whose full width at half maximum ranges from 5 degrees to 70 degrees is observed in azimuthal angle ranges, in a diffraction pattern of a grazing-incidence wide-angle X-ray scattering (GI-WAXS) spectrum, of −90 degrees to −70 degrees and 70 degrees to 90 degrees (the azimuthal angle is determined by setting an angle of out-of-plane diffraction pattern of the GIWAXS spectrum as 0 degrees), wherein a scattering vector ranges from 12 nm$^{-1}$ to 16 nm$^{-1}$:

Condition 2: A melting transition peak or an isotropic transition peak is produced in a range of −80° C. to 200° C. during DSC analysis:

Condition 3: A peak whose full width at half maximum ranges from 0.2 to 0.9 nm$^{-1}$ is observed when a scattering vector (q) ranges from 0.5 nm$^{-1}$ to 10 nm during X-ray diffraction (XRD) analysis:

Condition 4: The first block includes a side chain, wherein a number (n) of chain-forming atoms in the side chain and a scattering vector (q) during XRD analysis satisfy Mathematical Expression 1 below:

$$3 \text{ nm}^{-1} \text{ to } 5 \text{ nm}^{-1} = nq/(2 \times \pi) \quad \text{[Mathematical Expression 1]}$$

where in the Mathematical Expression 1, n represents a number of the chain-forming atoms included in the side chain, and q represents a smallest scattering vector (q) whose peak is detectable or a scattering vector (q) that is observed to have a peak with a largest peak area, during XRD analysis on the block copolymer.

2. The block copolymer of claim 1, wherein the first block produces both the melting transition peak and the isotropic transition peak according to the Condition 2, wherein a difference (Ti−Tm) between a temperature (Ti) at which the isotropic transition peak is produced and a temperature (Tm) at which the melting transition peak is produced is 5° C. to 70° C.

3. The block copolymer of claim 1, wherein the first block produces both the melting transition peak and the isotropic transition peak according to the Condition 2, wherein a ratio (M/I) of an area (M) of the melting transition peak to an area (I) of the isotropic transition peak ranges from 0.1 to 500.

4. The block copolymer of claim 1, wherein the first block produces the melting transition peak between −10° C. and 55° C., according to the Condition 2.

5. The block copolymer of claim 1, wherein the first block includes a side chain and satisfies Mathematical Expression 1 below, according to the Condition 2:

$$10° \text{ C.} \leq Tm - 12.25° \text{ C.} \times n + 149.5° \text{ C.}$$
$$\leq 10° \text{ C.} \quad \text{[Mathematical Expression 1]}$$

where in the Mathematical Expression 1, Tm represents a temperature at which the melting transition peak appears, and n represents the number of chain-forming atoms included in the side chain.

6. The block copolymer of claim 1, wherein X of Mathematical Expression 2 below is 1.25 or more:

$$X=1+(D \times M)/(K \times L) \quad \text{[Mathematical Expression 2]}$$

where in the Mathematical Expression A, D represents a ratio (D2/D1) of a density (D2) of the second block to a density (D1) of the first block;

M represents a ratio (M1/M2) of a molar mass (M1) of the first block to a molar mass (M2) of the second block;

K represents a ratio (A2/A1) in a $^1$H-NMR spectrum of an area (A2) of a peak that is produced based on the second block to an area (A1) of a peak that is produced based on the first block; and L represents a ratio (H1/H2) of a number (H1) of hydrogen atoms in 1 mole of a repeat unit of the first block to a number (H2) of hydrogen atoms in 1 mole of a repeat unit of the second block.

7. The block copolymer of claim 1, wherein the first block or the second block includes an aromatic structure.

8. The block copolymer of claim 1, wherein each of the first block and the second block includes an aromatic structure.

9. The block copolymer of claim 1, wherein the first block includes an aromatic structure without a halogen atom, and the second block includes an aromatic structure that includes one or more halogen atoms.

10. The block copolymer of claim 1, wherein the first block or the second block includes a side chain that includes 8 or more chain-forming atoms.

11. The block copolymer of claim 1, wherein the first block or the second block includes one or more halogen atoms.

12. The block copolymer of claim 1, wherein the first block includes a side chain with 8 or more chain-forming atoms, and the second block includes one or more halogen atoms.

13. The block copolymer of claim 1, wherein the first block or the second block includes an aromatic structure to which a side chain with 8 or more chain-forming atoms is connected.

14. The block copolymer of claim 13, wherein the side chain is connected to the aromatic structure by an oxygen atom or a nitrogen atom.

15. The block copolymer of claim 1, wherein the first block 1 or the second block includes an aromatic structure that is substituted in part by one or more halogen atoms.

16. The block copolymer of claim 1, wherein the first block includes an aromatic structure to which a side chain that includes 8 or more chain-forming atoms is connected, and the second block includes an aromatic structure that includes a halogen atom.

17. The block copolymer of claim 1, wherein the first block includes a side chain that includes 8 or more chain-forming atoms.

18. The block copolymer of claim 17, wherein the first block includes a ring structure that is substituted in part by a side chain.

19. The block copolymer of claim 18, wherein the ring structure does not include a halogen atom.

20. The block copolymer of claim 17, wherein the second block includes 3 or more halogen atoms.

21. The block copolymer of claim 20, wherein the second block includes a ring structure that is substituted in part by the halogen atoms.

22. The block copolymer of claim 1, wherein the first block includes a structural unit represented by Structural Formula 1 below:

[Structural Formula 1]

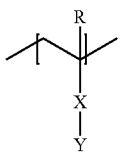

where in the Structural Formula 1, R represents a hydrogen atom or an alkyl group with 1 to 4 carbons;

X represents a single bond, an oxygen atom, a sulfur atom, $S(=O)_2$—, a carbonyl group, an alkylene group, an alkenylene group, an alkynylene group, —C(=O)—$X_1$— or —$X_1$—C(=O)—, wherein the $X_1$ represents an oxygen atom, a sulfur atom, —S(=O)$_2$—, an alkylene group, an alkenylene group or an alkynylene group; and Y represents a monovalent substituent that includes a ring structure to which a chain including 8 or more chain-forming atoms is connected.

23. The block copolymer of claim 1, wherein the second block includes a structural unit represented by Structural Formula 3 below:

[Structural Formula 3]

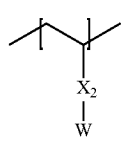

where in the Structural Formula 3, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, wherein the $X_1$ represents a single bond, an oxygen atom, a sulfur atom, —S(=O)$_2$—, an alkylene group, an alkenylene group or an alkynylene group; and W represents an aryl group that includes at least one halogen atom.

24. A polymer film comprising the block copolymer of claim 1, wherein the block copolymer is self-assembled.

25. A method of forming a polymer film comprising:
forming a polymer film that includes the block copolymer of claim 1 on a substrate, wherein the block copolymer is self-assembled.

26. A method of forming a pattern, the method comprising:
removing the first block or second block of the block copolymer of claim 1 from a polymer film that is formed on a substrate and includes the block copolymer, wherein the block copolymer is self-assembled.

* * * * *